United States Patent [19]

Horwell et al.

[11] Patent Number: 5,244,905

[45] Date of Patent: Sep. 14, 1993

[54] N-SUBSTITUTED CYCLOALKYL AND POLYCYCLOALKYL POLYHYDRO-β-CARBOLINE-PHENYLALANINE- AND PHENETHYLAMINE DERIVATIVES

[75] Inventors: David C. Horwell, Cambridge; Edward Roberts, Newmarket, both of England; Uwe Trostmann, March-Hugstetten, Fed. Rep. of Germany

[73] Assignee: Warner-Lambert Company, Morris Plains, N.J.

[21] Appl. No.: 726,651

[22] Filed: Jul. 12, 1991

Related U.S. Application Data

[63] Continuation-in-part of Ser. No. 576,297, Aug. 31, 1990, abandoned.

[51] Int. Cl.$^5$ .................... C07D 471/04; A61K 31/44
[52] U.S. Cl. ........................ 514/292; 546/86; 546/87
[58] Field of Search ............ 546/85, 86, 87; 514/292

[56] References Cited

U.S. PATENT DOCUMENTS

3,654,289  4/1972  Paris et al. .............. 546/85
3,862,160  1/1975  Martel et al. ............ 546/85
4,757,151  7/1988  Horwell ................... 548/469

FOREIGN PATENT DOCUMENTS

0336356 10/1989 European Pat. Off. ........... 209/42

OTHER PUBLICATIONS

*Brain Research*, 288 (1983) 199–211. G. W. Roberts et al., "Peptides, the Limbic Lobe and Schizophrenia".
*Brain Research*, 406 (1987) 130–135. B. A. MacVicar et al., "Inhibition of synaptic transmission in the hippocampus by . . . ".
*British Medical Bulletin*, (1982), v. 38, No. 3, pp. 253–258, G. J. Dockray, "The Physiology of Cholecystokinin in Brain and Gut".
*Cancer Research*, 46, 1612–1616, Apr. 1986, P. Singh et al., "Role of Gastrin and Gastrin Receptors on the Growth of a Transplantable . . . ".
*CCK in the Nervous System*, Ch. 7, pp. 110–127, M. J. Sheehan et al., (1984) "Central Actions of Cholecystokinin; Behavioural and Release Studies".
*Gastroenterology*, 1988; v. 95, No. 6, pp. 1541–1548, J. Palmer Smith et al., "Effects of Gastrin, Proglumide, and Somatostatin . . . ".
*Gastrointestinal Hormones*, 1980, Ch. 7, pp. 169–221, Viktor Mutt, "Cholecystokinin: Isolation, Structure, and Functions".
*Ibid.*, Ch. 22, pp. 507–527, Leonard R. Johnson, "Effect of Gastrointestinal Hormones on Growth of Gastrointestinal Tissue".
*Ibid.*, Ch. 23, pp. 529–564, Stanislaw J. Konturek, "Gastrointestinal Hormones and Gastric Secretion". (1980).
*Ibid.*, Ch. 30, pp. 729–739, Fl. Stadil, "Gastrinomas". (1986).
*Life Sciences*, v. 27, pp. 355–368, John E. Morley, "The Neuroendocrine Control of Appetite: The Role of the Endogenous Opiates . . . " (1980).

(List continued on next page.)

Primary Examiner—Alan L. Rotman
Attorney, Agent, or Firm—Elizabeth M. Anderson

[57] ABSTRACT

Novel substituted polyhydro-β-carboline derivatives useful as agents in the treatment of obesity, hypersecretion of gastric acid in the gut, gastrin-dependent tumors, or as antipsychotic agents are disclosed. Further the compounds are antianxiety agents and antiulcer agents. Further, the compounds are useful for treating and/or preventing panic attacks. They are agents useful for preventing the response to withdrawal from chronic treatment with or use of nicotine, caffeine, diazepam, alcohol, cocaine or opioids. Also disclosed are pharmaceutical compositions and methods of treatment using the compounds as well as processes for preparing them and novel intermediates useful in their preparation. An additional feature of the invention is the use of the subject compounds in diagnostic compositions.

21 Claims, No Drawings

OTHER PUBLICATION—Continued

*Journal of Neurochemistry*, v. 32, pp. 1339–1341, "Immunochemical Evidence of Cholecystokinin Tetrapeptides in Hog Brain". (1979).
*Neuropharmacology*, v. 26, No. 4, pp. 289–300, 1987, R. G. Hill, et al., "Antinociceptive Action of Cholecystokinin Octapeptide (CCK 8) . . . ".
*Journal of Neuroscience*, Mar. 1988, 8(3):988–1000, H. Demeulemeester, et al., "Heterogeneity of GABAergic Cells in Cat Visual Cortex".
*Neuroscience*, v. 19, No. 1, pp. 181–192, 1986, S. Totterdell et al., "Cholecystokinin-immunoreactive Boutons in Synaptic Contact . . . ".
*Peptides*, v. 4, pp. 749–753, 1983, L. H. Schneider et al., "CCK-8 Modulation of Mesolimbic Dopamine: Antagonism of Amphetamine- . . . ".
Goodman and Gilman's *The Pharmacological Basis of Therapeutics*, 7th ed. (1985), Ch. 17, S. C. Harvey, "Hypnotics and Sedatives".
*Pharmacology Biochemistry & Behaviour*, v. 30, pp. 309–317, 1988, Friedbert Weiss, et al., "Opposite Actions of CCK-8 on . . . ".
*Regulatory Peptides*, 14, (1986) 277–291, R. R. Schick et al., "Intracerebroyentricular injections of cholecystokinin . . . ".
*Science*, v. 206, Oct. 26, 1979, pp. 471–473, "Cholecystokinin Octapeptide: Continuous Picomole Injections into the Cerebral . . . ".
*Trends in Pharmacological Sciences*, v. 11, Jul. 1990, pp. 271–273, "Cholecystokinin and Anxiety".

N-SUBSTITUTED CYCLOALKYL AND POLYCYCLOALKYL POLYHYDRO-β-CARBOLINE-PHENYLALANINE- AND PHENETHYLAMINE DERIVATIVES

This application is a continuation-in-part of U.S. Ser. No. 07/576,297, filed Aug. 31, 1990, now abandoned.

BACKGROUND OF THE INVENTION

Agents acting at central cholecystokinin (CCK) receptors may induce satiety (Schick, Yaksh and Go, *Regulatory Peptides* 14:277-291, 1986). They are also expected to act as analgesics (Hill, Hughes and Pittaway, *Neuropharmacology* 26:289-300, 1987), and as anticonvulsants (MacVicar, Kerrin and Davison, *Brain Research*, 406:130-135, 1987).

Reduced levels of CCK-peptides have been found in the brains of schizophrenic patients compared with controls (Roberts, Ferrier, Lee, Crow, Johnstone, Owens, Bacarese-Hamilton, McGregor, O'Shaughnessey, Polak and Bloom. *Brain Research* 288, 199-211, 1983). It has been proposed that changes in the activity of CCK neurones projecting to the nucleus accumbens may play a role in schizophrenic processes by influencing dopaminergic function (Totterdell and Smith, *Neuroscience* 19, 181-192, 1986). This is consistent with numerous reports that CCK peptides modulate dopaminergic function in the basal ganglia and particularly the nucleus accumbens (Weiss, Tanzer, and Ettenberg, *Pharmacology, Biochemistry and Behaviour* 30, 309-317, 1988; Schneider, Allpert and Iversen, *Peptides* 4, 749-753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence and CCK peptides can bind to the gastrin receptor of the stomach mucosa and elicit acid secretion in many species including human (Konturek, *Gastrointestinal Hormones*, Ch. 23, pp 529-564, 1980, ed. G. B. J. Glass, Raven Press, NY). Antagonists of the CCK-B receptor would also be expected to be antagonists at the stomach gastrin receptor and this would also be of value for conditions involving excessive acid secretion.

CCK and gastrin peptides have trophic effects on the pancreas and various tissues of the gastro-intestinal tract (Johnson, ibid., pp 507-527), actions which are associated with increased DNA and RNA synthesis. Moreover, gastrin secreting cells are associated with certain gastrointestinal tumors as in the Zollinger-Ellison syndrome (Stadil, ibid., pp 729-739), and some colorectal tumors may also be gastrin/CCK dependent (Singh, Walker, Townsend and Thompson, *Cancer Research*, 46, 1612 (1986), and Smith, J. P., *Gastroenterology*, 95, 1541 (1988)). Antagonists of CCK/gastrin receptors could therefore be of therapeutic value as antitumor agents.

The CCK peptides are widely distributed in various organs of the body including the gastrointestinal tract, endocrine glands, and the nerves of the peripheral and central nervous systems. Various biologically active forms have been identified including a 33-amino acid hormone and various carboxyl terminus fragments of this peptide (e.g., the octapeptide CCK26-33 and the tetrapeptide CCK30-33). (G. J. Dockray, *Br. Med. Bull.*, 38 (No. 3):253-258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions and other behavioral effects. ("Cholecystokinin: Isolation, Structure and Functions," G. B. J. Glass, Ed., Raven Press, New York, 1980, pp 169-221; J. E. Morley, *Life Sciences* 27:355-368, 1980; "Cholecystokinin in the Nervous System," J. de Belleroche and G. J. Dockray, Ed., Ellis Horwood, Chichester, England, 1984, pp 110-127.)

The high concentrations of CCK peptides in many brain areas also indicate major brain functions for these peptides (G. J. Dockray, *Br. Med. Bull.*, 38 (No. 3):253-258, 1982). The most abundant form of brain CCK found is CCK26-33, although small quantities of CCK30-33 exist (Redfeld and Gotterman, *J. Neurochem.*, 32:1339-1341, 1979). The role of central nervous system CCK is not known with certainty, but it has been implicated in the control of feeding (Della-Fera and Baile, *Science* 206:471-473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (H. Demeulemeester et al, *J Neuroscience* 8, 988-1000, 1988). Agents that modify GABA action may have utility as anxiolytic or hypnotic agents (S. C. Harvey, *The Pharmacological Basis of Therapeutics* (7th ed.) 1985, pp 339-371, MacMillan). Thus, agents which modify CCK action may have parallel anxiolytic or hypnotic activities.

The role of CCK in anxiety is disclosed in *TIPS*, 11, 271-273 (1990).

SUMMARY OF THE INVENTION

The invention relates to novel compounds of the formula

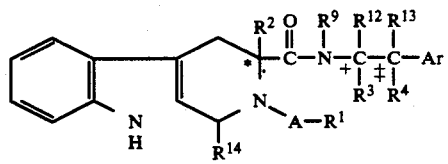

and the pharmaceutically acceptable salts thereof wherein $R^1$, $R^2$, $R^3$, $R^4$, $R^9$, $R^{12}$, $R^{13}$, $R^{14}$, A and Ar are as defined hereinbelow.

In commonly assigned copending applications 07/576,308; 07/576,628; 07/576,296; 07/576,315; 07/576,024 filed on even date herewith by Horwell, et al, the disclosures of which are herein incorporated by reference, CCK antagonists are disclosed.

The invention also relates to a pharmaceutical composition containing an effective amount of a compound according to formula I in combination with a pharmaceutically acceptable carrier in unit dosage form effective for appetite suppression.

The compounds are also useful as anxiolytics, antipsychotics, especially for treating schizophrenic behavior, as agents in treating disorders of the extrapyramidal motor system, as agents for blocking the trophic and growth stimulating actions of CCK and gastrin, and as agents for treating gastrointestinal motility.

Compounds of the invention are also useful as analgesics and potentiate the effect of morphine. They can be used as an adjunct to morphine and other opioids in the treatment of severe pain such as cancer pain and reduce the dose of morphine in treatment of pain where morphine is contraindicated.

An additional use for compounds is that the suitable radiolabeled iodine-127 isotope gives an agent suitable for treatment of gastrin dependent tumors such as those found in colonic cancers. I-125 radiolabeled compounds of the invention can also be used as a diagnostic agent by localization of gastrin and CCK-B receptors in both peripheral and central tissue.

The invention further relates to a method of appetite suppression in mammals which comprises administering an amount effective to suppress appetite of the composition described above to a mammal in need of such treatment.

The invention also relates to a pharmaceutical composition for reducing gastric acid secretion containing an effective amount of a compound of formula I in combination with a pharmaceutically acceptable carrier in unit dosage form effective for reducing gastric acid secretion.

The invention also relates to a method for reducing gastric acid secretion in mammals which comprises administering an amount effective for gastric acid secretion reduction of the composition described above to a mammal in need of such treatment.

The invention also relates to a pharmaceutical composition containing an effective amount of a compound of formula I in combination with a pharmaceutically acceptable carrier in unit dosage form effective for reducing anxiety.

The invention also relates to a method for reducing anxiety in mammals which comprises administering an amount effective for anxiety reduction of the composition described above to a mammal in need of such treatment.

The invention also relates to a pharmaceutical composition containing an effective amount of a compound of formula I in combination with a pharmaceutically acceptable carrier in unit dosage form effective for treating gastrointestinal ulcers.

The invention further relates to a method for treating gastrointestinal ulcers in mammals which comprises administering an amount effective for gastrointestinal ulcer treatment of the composition as described above to a mammal in need of such treatment.

The invention also relates to a pharmaceutical composition containing an effective amount of a compound of formula I in combination with a pharmaceutically acceptable carrier in unit dosage form effective for treating psychosis, i.e., schizophrenia.

The invention further relates to a method for treating psychosis in mammals which comprises administering an amount effective for treating psychoses of a composition as described above to a mammal in need of such treatment.

The invention also relates to pharmaceutical compositions effective for stimulating or blocking CCK or gastrin receptors, for altering the activity of brain neurons, for schizophrenia, for treating disorders of the extrapyramidal motor system, for blocking the trophic and growth stimulating actions of CCK and gastrin, and for treating gastrointestinal motility.

The invention also relates to a pharmaceutical composition for preventing the withdrawal response produced by chronic treatment or abuse of drugs or alcohol.

The invention further relates to a method for treating the withdrawal response produced by withdrawal from chronic treatment or withdrawal from abuse of drugs or alcohol. Such drugs include benzodiazepines, especially diazepam, cocaine, alcohol, caffeine, nicotine and opioids. Withdrawal symptoms are treated by administration of an effective withdrawal treating amount of a compound of the instant invention.

The invention also relates to a pharmaceutical composition containing an effective amount of a compound of formula I in combination with a pharmaceutically acceptable carrier in unit dosage form effective for treating and/or preventing panic.

The invention also relates to a method for treating and/or preventing panic in mammals which comprises administering an amount effective for panic treatment and/or prevention of the composition described above to a mammal in need of such treatment.

The invention further relates to the use of the compounds of formula I to prepare pharmaceutical and diagnostic compositions for the treatment and diagnosis of the conditions described above.

The invention further provides processes for the preparation of compounds of formula I.

The invention further provides novel intermediates useful in the preparation of compounds of formula I and also provides processes for the preparation of the intermediates.

DETAILED DESCRIPTION

The compounds of the present invention are formed by the condensation of two modified amino acids and are therefore not peptides. Rather they are "dipeptoids", synthetic peptide-related compounds differing from natural dipeptides.

The compounds of the present invention are represented by the formula or a pharmaceutically acceptable salt thereof wherein:

$R^1$ is tert.-butyl, a cyclo- or polycycloalkyl hydrocarbon of from three to twelve carbon atoms with from zero to four substituents, each independently selected from the group consisting of: a straight or branched alkyl of from one to six carbon atoms, halogen, CN, OR*, SR*, CO₂R*, CF₃, NR⁵R⁶, or —(CH₂)ₙOR⁵, wherein R* is hydrogen, straight or branched alkyl of from one to six carbon atoms, R⁵ and R⁶ are each independently hydrogen or alkyl of from one to six carbon atoms; and n is an integer from zero to six;

A is —(CH₂)ₙCO—, —SO₂—, —SO—, —NHCO—,

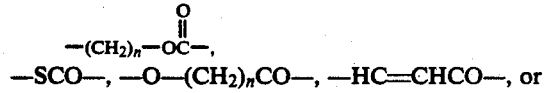

—SCO—, —O—(CH₂)ₙCO—, —HC=CHCO—, or

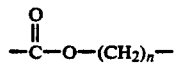

wherein n is an integer from zero to six;

R² is hydrogen, a straight or branched alkyl of from one to six carbon atoms, —HC=CH₂, —C≡CH, —CH₂—CH=CH₂, —CH₂C≡CH, —(CH₂)ₙAr, —(CH₂)ₙOR*, —(CH₂)ₙOAr, —(CH₂)ₙCO₂R*, —(CH₂)ₙNR⁵R⁶ wherein n, R* R⁵ and R⁶ are as defined above and Ar is as defined below;

R³, R⁴ and R¹⁴ are each independently selected from hydrogen, R², and —(CH₂)ₙ′—B—D, wherein n′ is an integer of from zero to three;

B is a bond
—OCO(CH₂)ₙ—
—O(CH₂)ₙ—
—NHCO(CH₂)ₙ—
—CONH(CH₂)ₙ—
—NHCOCH=CH—
—COO(CH₂)ₙ—
—CO(CH₂)ₙ—
—S(CH₂)ₙ—
—SO(CH₂)ₙ—
—SO₂(CH₂)ₙ—
—NHSO₂(CH₂)ₙ—,
—SO₂NH(CH₂)ₙ—,

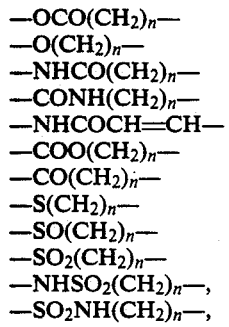

wherein R⁷ and R⁸ are independently selected from hydrogen and R² or together form a ring (CH₂)ₘ wherein m is an integer of from 1 to 5 and n is as defined above;

D is
—COOR*,
—CH₂OR*,
—CHR²OR*,
—CH₂SR*,
—CHR²SR*,
—CONR⁵R⁶,
—CN,
—NR⁵R⁶,
—OH,
—H, and
acid replacements such as tetrazole,

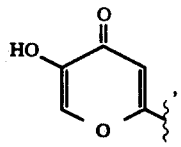

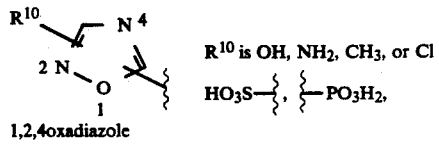 R¹⁰ is OH, NH₂, CH₃, or Cl

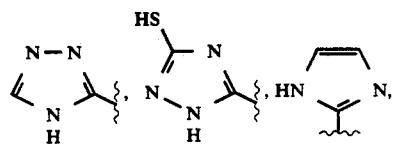

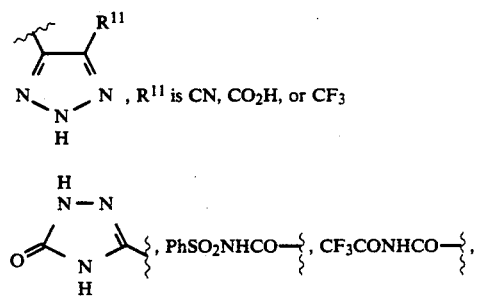

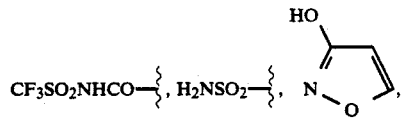

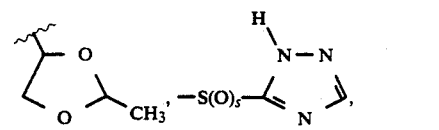

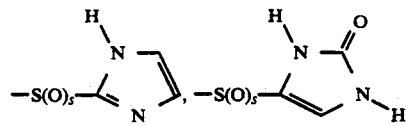

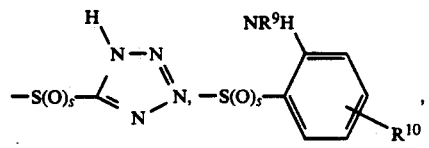

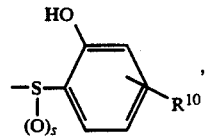

wherein R*, R², R⁵, and R⁶ are as defined above and s is an integer of from 0 to 2;

$R^9$ is H, or a straight or branched alkyl of from one to six carbon atoms, —$(CH_2)_nCO_2R^*$, $(CH_2)_nOAr'$, $(CH_2)_nAr'$, $(CH_2)_nNR^5R^6$, wherein n, $R^*$, $R^5$, and $R^6$ are as defined above or taken from $R^3$ and $Ar'$ is taken from Ar as defined below;

$R^{12}$ and $R^{13}$ can each be independently hydrogen or can each be taken with $R^3$ and $R^4$ respectively to form a moiety doubly bonded to the carbon atom (in which case the carbon atom is not chiral); and Ar is a mono- or polycyclic unsubstituted or substituted carbo- or heterocyclic aromatic or hydroaromatic moiety.

Preferred Ar is 2 or 3 -thienyl, 2 or 3-furanyl, 2, 3 or 4-pyridinyl or an unsubstituted or substituted benzene ring

wherein E and F are each independently $R^3$ as defined above, hydrogen, fluorine, chlorine, bromine, iodine, methyl, methoxy, trifluoromethyl or nitro.

Especially preferred Ar is from $R^3$ as defined as the ortho (2-) position of the ring, for example,

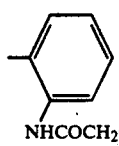 or 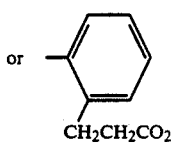

Preferred cycloalkyl or polycycloalkyl substituents have from six to ten carbon atoms.

Preferred compounds of the instant invention are those wherein cycloalkyl is a substituted or unsubstituted

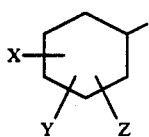

and wherein polycycloalkyl is selected from

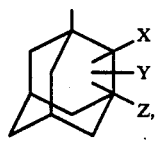 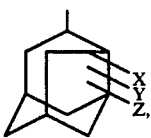

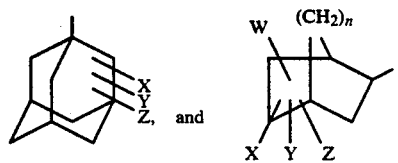

wherein W, X, Y, and Z are each independently hydrogen, a straight or branched alkyl of from one to six carbon atoms, $CF_3$, $NR^5R^6$, —$(CH_2)_nCO_2R^*$, or CN, F, Cl, Br, $OR^*$, $SR^*$, wherein $R^*$ is hydrogen or a straight or branched alkyl of from one to six carbon atoms and $R^5$ and $R^6$ are as defined above and n is an integer of from 1 to 3.

Other preferred compounds of the instant invention are those wherein $R^1$ is tert.-butyl, 2-adamantyl or 1-(S)-2-endobornyl;
A is —NHCO—, —OCO—, —$SO_2$—, —S(=O)— or —$CH_2CO$—;
$R^2$ is H, —$CH_3$, —$CH_2CO_2CH_3$ or —$CH_2C\equiv CH$;
$R^3$ is —$(CH_2)_n$—B—D or H;
$R^4$ is —$(CH_2)_{n'}$—B—D or H; and
$R^9$ is hydrogen or methyl.

More preferred compounds of the instant invention are those wherein $R^1$ is tert.-butyl or 2-adamantyl,
A is

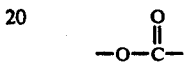

or —$SO_2$—NH—,
$R^2$ is H or —$CH_3$,
$R^3$ is H, —$CH_2OH$, —$CO_2H$, —$CH_2CH_2CO_2H$, —$CH_2NHCOCH_2CH_2CO_2H$, —$CH_2CO_2H$, or —$CH_2NHCOCH=CHCO_2H$;
$R^4$ is H, $NH_2$, —$NHCOCH_2CH_2CO_2H$, —$NHCOCH_2CH_2COCH_2C_6H_5$, —$NHCOCH_2CO_2H$, —$NHCOCH=CHCO_2H$, —$OCOCH_2CH_2CO_2H$, —$CH_2CO_2H$, —$CH_2SCH_2CO_2H$, —$CH_2SCH_2CH_2CO_2H$,

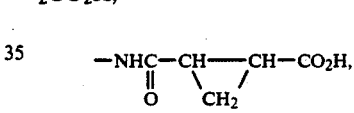

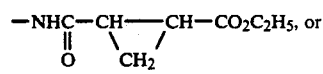

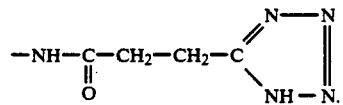

Each of the substituents and/or moieties cited in the preferred groups is itself preferred, so that the invention likewise applies to combinations of individually preferred substituents and/or moieties with substituents and/or moieties of other groups as disclosed in the invention.

Most preferred compounds of the instant invention are:

1. (+/−)1,3,4,9-tetrahydro-3-methyl-3-[[2-phenylethyl)amino]carbonyl]-2H-pyrido[3,4-b]indole-2carboxylic acid, tricyclo[3.3.1.1$^{3,7}$]dec-2-yl ester;

2. (R)-1,3,4,9-tetrahydro-3-methyl-3-[[2-phenylethyl)amino]carbonyl]-2H-pyrido[3,4-b]indole-2carboxylic acid, tricyclo[3.3.1.1$^{3,7}$]dec-2 yl ester.

3. (S)-1,3,4,9-tetrahydro-3-methyl-3-[[2-phenylethyl)amino]carbonyl]-2H-pyrido[3,4-b]indole-2carboxylic acid, tricyclo[3.3.1.13,7]dec-2-yl ester;

4. 1,3,4,9-tetrahydro-3-[[[1-(hydroxymethyl)-2-phenylethyl]amino]carbonyl]-3-methyl 2H-pyrido[3,4-b]indole 2-carboxylic acid,tricyclo[3.3.1.1$^{3,7}$]dec-2-yl ester (mixture of diastereomers);

5. (R)-1,3,4,9-tetrahydro-3-[[[1-(hydroxymethyl)-2-phenylethyl]amino]carbonyl]-3-methyl-2H-pyrido[3,4-b]-indole-2-carboxylic acid,tricyclo[3.3.1.1³,⁷]dec-2-yl ester;
6. (S)-1,3,4,9-tetrahydro-3-[[[1-(hydroxymethyl)-2-phenylethyl]amino]carbonyl]-3-methyl-2H-pyrido[3,4 b]indole-2-carboxylic acid, tricyclo[3.3.1.1³,⁷]dec-2-yl ester;
7. 1,3,4,9-tetrahydro-3-[[[1-(hydroxymethyl)-2-hydroxy-2-phenylethyl]amino]carbonyl]-3-methyl-2H-pyrido[3,4-b]indole-2-carboxylic acid, tricyclo[3.3.1.1³,⁷]dec-2-yl ester;
8. 3-[[(2-amino-2-phenylethyl)amino]carbonyl]1,3,4,9-tetrahydro-3-methyl]-2H-pyrido[3,4-b]indole-2carboxylic acid, tricyclo[3.3.1.1⁵,⁷]dec-2-yl ester, (mixtures of diastereomers);
9. 3-[[[2-(3-carboxy-1-oxopropyl) amino]-2phenylethyl]amino]carbonyl]-1,3,4,9-tetrahydro-3-methyl-2H-pyrido[3,4 b]indole-2-carboxylic acid, tricyclo[3.3.1.1³,⁷]dec-2-yl ester, [R-(R*,R*)] and [R-(R*,S*)]-;
10. 3-[[[2-(R)-(3-carboxy-1-oxopropyl)amino]-2-phenylethyl]amino]carbonyl]-1,3,4,9-tetrahydro-3-(S)-methyl-2H-pyrido[3,4-b]indole-2-carboxylic acid, tricyclo[3.3.1.1³,⁷]dec-2-yl ester;
11. 3-[3-[3 [2-[2-[1,4-dioxo-4-(phenylmethoxy)butyl]amino]-2-phenylethyl]amino]carbonyl]-1,3,4,9-tetrahydro-3-methyl]-2H-pyrido[3,4-b]indole-2carboxylic acid, tricyclo[3.3.1.1⁵,⁷]dec-2-yl ester (mixture of diastereomers);
12. 3-[[(2 hydroxy-2-phenylethyl)amino]carbonyl]-1,3,4,9-tetrahydro-3-methyl]-2H-pyrido[3,4-b]indole-2-carboxylic acid, tricyclo[3.3.1.1⁵,⁷]dec-2-yl ester;
13. butanedioic acid,mono[2-[[[2,3,4,9-tetrahydro-3-methyl-2[(tricyclo[3.3.1.1³,⁷]dec-2-ylox)carbonyl]-1H-pyrido[3,4-b]indole-3-yl]carbonyl]amino]-1-phenethyl] ester;
14. 3-[[[2-[(3-carboxyacetyl)amino]-2-phenethyl]amino]carbonyl]-1,3,4,9-tetrahydro-3-methyl-2H-pyrido[3,4-b]indole-2-carboxylic acid, [tricyclo[3.3.1.1³,⁷]dec-2-yl ester (mixture of diastereomers);
15. 3-[[[2-[(3-carboxy-1-oxo-2-propenyl)amino]-2-phenethyl]amino]carbonyl]1,3,4,9-tetrahydro-3-methyl-2H-pyrido[3,4-b]indole-2-carboxylic acid, tricyclo[3.3.1.1³,⁷]dec 2-yl ester (mixture of diastereomers);
16. 3-[[[1-[[(3-carboxy-1-oxopropyl)amino]methyl]-1-phenethyl]amino]carbonyl]-1,3,4,9-tetrahydro-3-methyl-2H-pyrido[3,4-b]indole-2-carboxylic acid, [tricyclo[3.3.1.1³,⁷]dec-2-yl ester (mixture of diastereomers);
17. (+/−)-1,3,4,9-tetrahydro-3-[[(2-phenethyl)amino]-carbonyl]-2H-pyrido[3,4-b]indole-2-carboxylic acid, [tricyclo[3.3.1.1³,⁷]dec-2-yl ester;
18. 3-[[(1-carboxy-2-phenethyl)amino]carbonyl]-1,3,4,9-tetrahydro-2H-pyrido[3,4-b]indole-2-carboxylic acid, 1,1-dimethylethyl ester;
19. (+/−)-1,3,4,9-tetrahydro-3-methyl-N-(2-phenylethyl)-2-[(tricyclo[3.3.1.1³,⁷]dec-2-ylamino)sulfonyl]1H-pyrido[3,4-b]indole-3-carboxamide;
20. 3-[[[3-carboxy-1-(phenylmethyl)propyl]amino]-carbonyl]-1,3,4,9-tetrahydro-3-methyl-2H-pyrido-[3,4-b]indole-2-carboxylic acid, tricyclo-[3.3.1.1³,⁷]dec-2-yl ester;
21. 1,3,4,9 tetrahydro-3-methyl-3-[[[2-[[1-oxo-3-(1H-tetrazol-5-yl)propyl]amino]-2-phenethyl]amino]carbonyl]-2H-pyrido[3,4-b]indole-2-carboxylic acid, tricyclo[3.3.1.1³,⁷]dec-2-yl ester; and
22. 3-[[[2 [[(2-carboxy-1-cyclopropyl)carbonyl]amino]-2-phenethyl]amino]carbonyl]-1,3,4,9-tetrahydro-3-methyl-2H-pyrido[3,4-b]indole-2-carboxylic acid ethyl ester, tricyclo[3.3.1.1³,⁷]dec 2-yl ester.

Table I illustrates representative compounds of the invention. The numbers on the left hand column correspond to the compound numbers given above.

The compounds include solvates and hydrates and pharmaceutically acceptable salts of the compounds of formula I.

The compounds of the present invention can have multiple chiral centers including those designated in the above formula I by an *, †, ‡, depending on their structures. For example, when $R^3$ taken with $R^{12}$ and $R^4$ taken with $R^{13}$ form double bonds to these carbon atoms they are no longer chiral. In addition, centers of asymmetry may exist on substituents $R^1$, $R^9$, $R^3$, $R^4$, $R^{14}$ and/or Ar. In particular the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by convention method well known in the art such as conversion to a salt with an optically active compound, followed by separation by chromatography or recrystallization and reconversion to the nonsalt form.

The compounds of the present invention can be formed by coupling individual substituted α-amino acids by methods well known in the art. (See, for example, standard synthetic methods discussed in the multivolume treatise "The Peptides, Analysis, Synthesis, Biology," by Gross and Meienhofer, Academic Press, New York.) The individual substituted alpha amino acid starting materials are generally known or, if not known, may be synthesized and, if desired, resolved by methods within the skill of the art. (Synthesis of racemic [DL]-α-methyl tryptophan methyl ester—see Brāna, M. F., et al, *J. Heterocyclic Chem.*, 1980, 17:829.)

Compounds of the general formula I are prepared according to reaction scheme I by reacting compounds of the general formula II

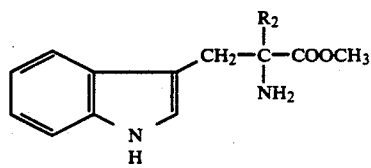

wherein $R^2$ is as defined above, with $R^{14}$—CHO in the presence of a base, to give compounds of the general formula III

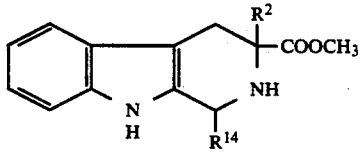

wherein R² and R¹⁴ are as defined above, which is reacted with a compound of general formula IV

wherein R¹ and A have the above given meaning, preferred R¹ substituents are 1-adamantyl, 2-adamantyl, 4-protoadamantyl, 9-methylenefluorenyl, exo-bornyl, endo-bornyl, exo-norbornyl, endo-norbornyl, 2-chlorocyclohexyl, 2-methylcyclohexyl, camphoryl, tert.-butyl, to give a compound of the general formula V

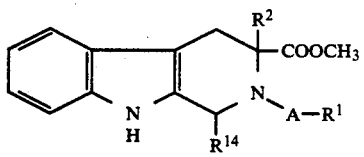

wherein R¹, R², R¹⁴ and A have the above given meaning, which is thereafter reacted with potassium hydroxide to give a compound of general formula VI

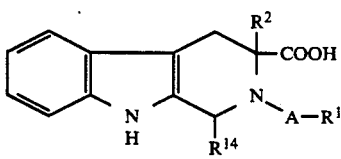

which are key intermediates (2) for preparing compounds of formula I with an desired amine of general formula VII

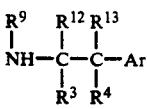

wherein R³, R⁴, R⁹, R¹², R¹³ and Ar are defined above.

Scheme I below illustrates procedures for preparing key intermediate (2) useful in producing final products of formula I.

SCHEME I

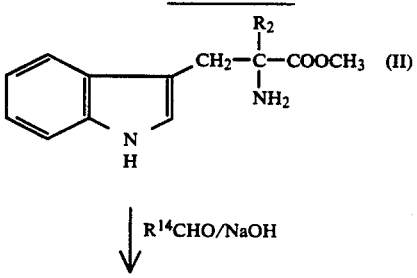

-continued
SCHEME I

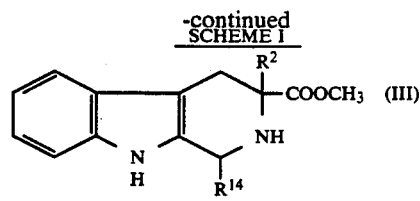

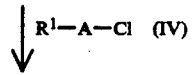

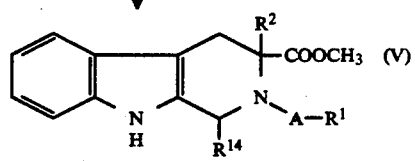

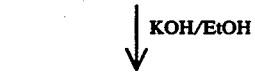

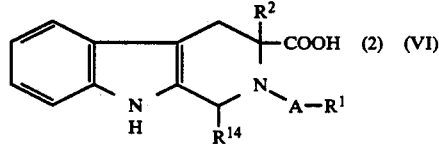

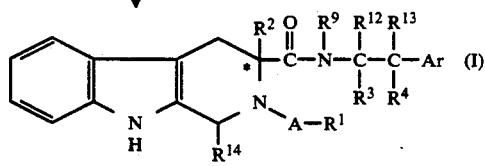

Scheme II below illustrates processes for the preparation of compounds of formula I using key intermediate, compound (2) from the Scheme I.

One process, as illustrated by sequence 2, 13, 14, involves reacting [(2-adamantyloxycarbonyl 3-methyl-9H-1,2,3,4-tetrahydro-β-carboline-3-yl]carboxylic acid methyl ester with dicyclohexylcarbodiimide (DCCI) and 1-hydroxybenzotriazole (HOBT) in ethyl acetate solution.

Subsequent addition of 2-amino-1-phenyl ethanol produces an alcohol as in compound (13) of the scheme. This alcohol may then be reacted with succinic anhydride to yield compound (14).

Another process of the invention is illustrated by sequence 2, 16, 15 of Scheme II. In this process intermediate (2) is reacted with N-methyl-morpholine and isobutyl-chloroformate in THF at −10° C. After stirring for an hour at that temperature the mixture is reacted with L phenylalaninol to yield a compound (16). This may then be reacted with succinic anhydride and DMAP to yield a compound as illustrated by (15).

In the sequence 2, 21, 22 intermediate (2) in solution is treated with N,N'-carbonyldiimidazole. This solution is stirred for two hours at room temperature. This reacts with 2-phenylethylamine to produce compound (21). This compound is converted to the free amine (22) by reaction with HCl solution. This can be treated with a substituted chloroformate to produce the desired amide (21).

In another process, sequence 2, 16, 17, and then 18, or 19 or 20, compound (12) may be converted to compound (16). The amide (16) may be converted to a free amine (17) by reaction with 20% pyridine in DMF.

A solution of the amine (17) may be reacted with a substituted acetylchloride to form the corresponding substituted acylamide (18).

Alternatively, a solution of free amine (17) may be reacted with a substituted sulphonylchloride to form the corresponding sulphonamide (19).

Additionally a solution of free amine (17) may be reacted with a substituted isocyanate to produce a desired compound (20). This may be converted, if desired, to a pharmaceutically acceptable salt.

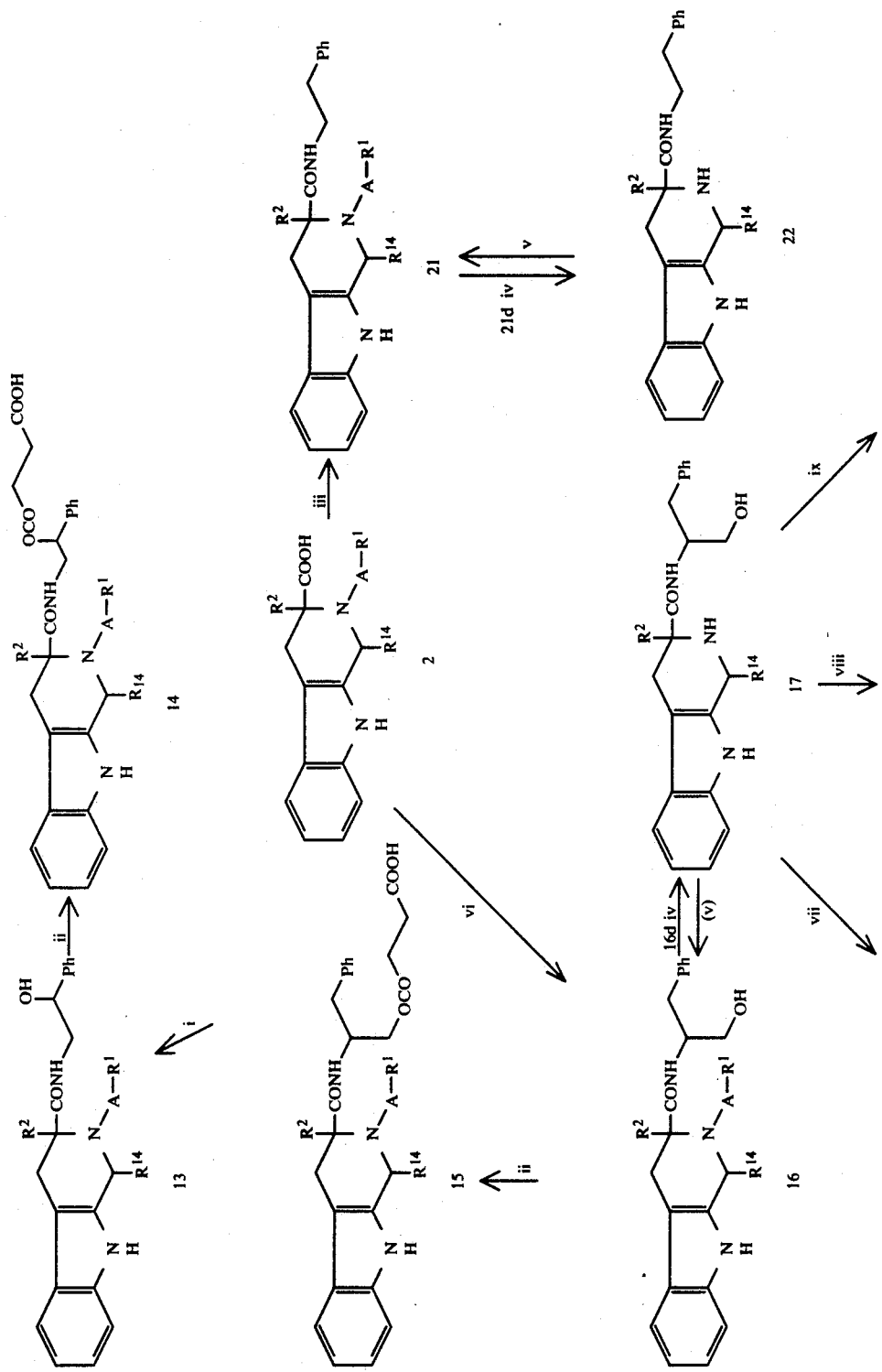
SCHEME II

-continued
SCHEME II
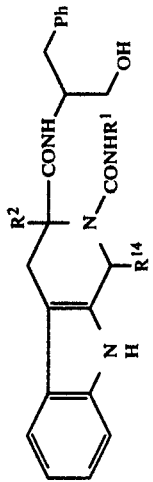
18
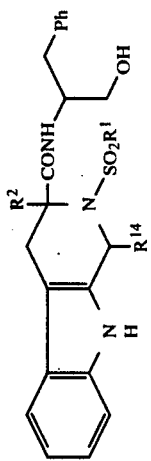
19
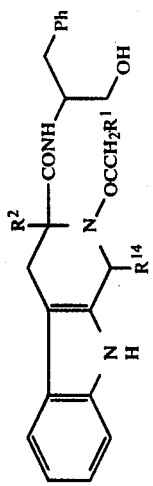
20
KEY
(i) DCCI, HOBT, (+) or (−) 2-amino-1-phenyl ethanol
(ii) Succinic anhydride, DMAP
(iii) CDI, 2-phenethylamine
(iv) HCl
(v) ROCOCl
(vi) N-methylmorpholine, isobutyl-chloroformate, L-phenylalaninol
(vii) $R^1$-acetylchloride
(viii) $R^1$-sulphonylchloride
(ix) $R^1$ isocyanate Scheme III below illustrates processes for preparing compounds of formula I.

One process is indicated by the sequence 2, 23, 24 of the scheme. The [(2N-adamantyloxycarbonyl-3-methyl- Also compound (26) may be reacted with fumaryl dichloride to produce compound (27).

Compound (27) or (28) may be converted, if desired, to a pharmaceutically acceptable salt thereof.

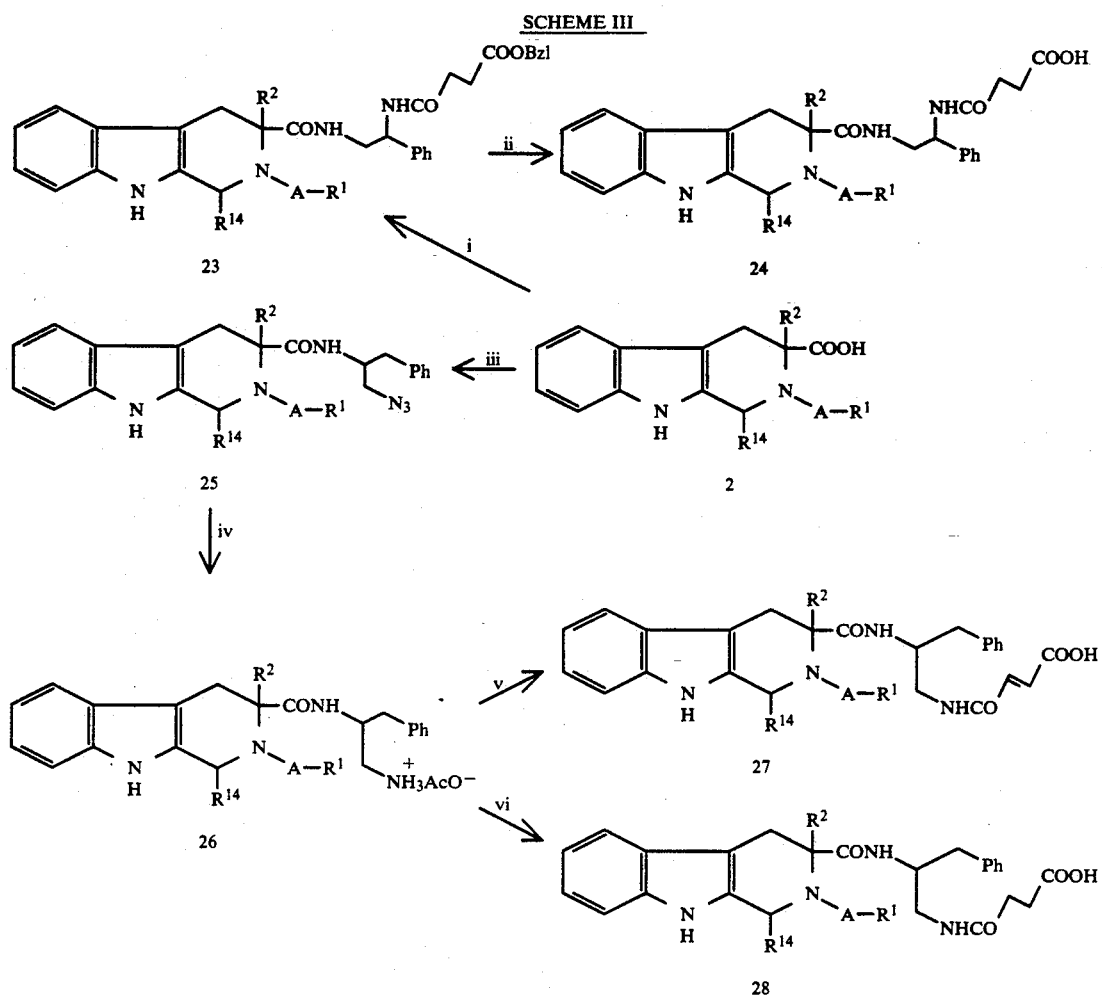

KEY
(i) 12, N-methylmorpholine, isobutyl-chloroformate
(ii) 10% Pd/C, EtOH
(iii) 6, DCCI, PFP
(iv) 10% Pd/C, 1% AcOH in EtOH
(v) i. Fumaryl dichloride ii. OH⁻
(vi) Succinic anhydride, DMAP 9H-1,2,3,4-tetrahydro-β-carboline-3-yl]carboxylic acid methyl ester intermediate in ethyl acetate is treated sequentially with N-methylmorpholine and isobutyl chloroformate and later reacted with an amine to produce a desired benzyl ester (23). This is reduced to the free carboxylic acid (24) using hydrogen and a 10% palladium on carbon catalyst for about 4 hours. The reaction mixture is filtered, washed and concentrated in vacuo to yield (24).

Another process is illustrated by sequence 2, 25, 26 and 27 or 28. Compound (2) may be reacted with DCCI and PFP in ethyl acetate and thereafter with an aminoazide to yield a compound (25). This may then be converted to a crude amine acetate (26) by hydrogenation in the presence of a catalyst such as ten percent palladium in carbon.

Compound (26) may then be reacted with succinic anhydride to form the free carboxylic acid (28).

Scheme IV below illustrates synthesis of preferred C-terminal side chains $R^3$ and $R^4$ used to prepare the final products illustrated in Scheme V.

Thus the conversion of (35) to (37) is may be done by condensing the isobutylformyl ester of (35) with 2-(trimethylsilyl)ethanol to give intermediate (36) followed by cleavage of the TMS group with TFA to give (37).

The oxime ester intermediate (40) may be prepared by acylation of aminoacetophenone hydrochloric acid (38) with 2-(trimethylsilyl)ethylchloroformate in THF following by condensation with hydroxylamine hydrochloride and sodium acetate to give an oxime. Compound (39) may be prepared by adding methyl bromoacetate in the presence of 10% NaOH and TBAB in toluene. The trimethylsilylethyl group may be then selectively removed with tetrabutylammonium fluoride.

Intermediate (42) may be prepared from the alcohol (41) in the steps involving tosylation of the alcohol, displacement of the tosylate by sodium azide in DMF followed by catalytic reduction.

The tetrazole carboxylic acid intermediate (44) may be prepared from the nitrile (43) in three steps by addition of azide to form a tetrazole which is protected by benzylation followed by hydrolysis of the methyl ester to the free carboxylic acid using an aqueous THF solution of lithium hydroxide.

The diene ester (47) may be prepared from the BOC-protected phenylalanine (45) through aldehyde (46) using the Wittig reagent $Ph_3P\!=\!CHCH\!=\!CHCO_2CH_3$.

The intermediate ether (50) may be prepared from the chlorohydroxy compound (48) involving displacement of the chloride with sodium azide followed by alkylation of the anion of the hydroxyl group with methyl iodoacetate to give the azido ether (49) which may be then reduced under catalytic conditions.

The ethyl ester (52) may be prepared by catalytic hydrogenation of nitrile (51).

SCHEME IV

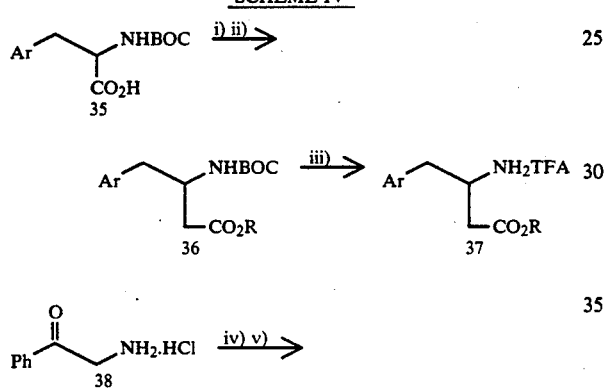

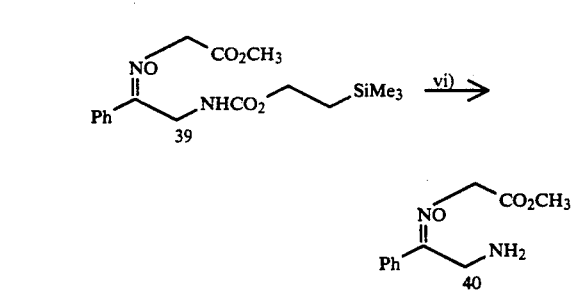

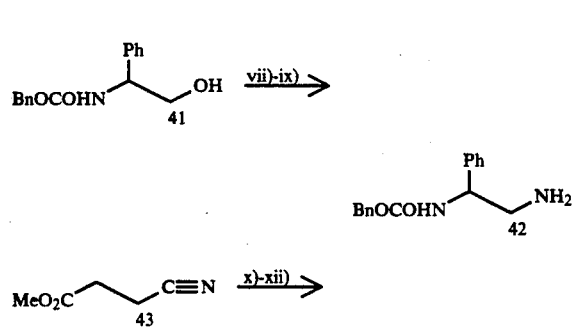

-continued
SCHEME IV

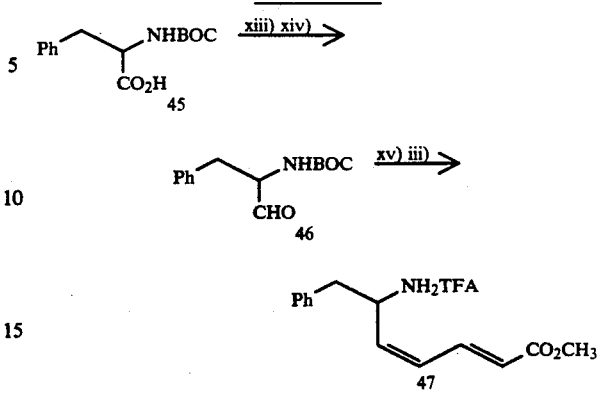

R is methyl, when Ar is phenyl.
R is 2-(trimethylsilyl)ethyl when Ar is p-iodo phenyl.
KEY
(i) N-methyl morpholine, isobutylchloroformate, THF then diazomethane;
(ii) Silver benzoate, Et₃N, then MeOH or 2-(trimethylsilyl)ethanol or benzyl alcohol;
(iii) TFA, CH₂Cl₂;
(iv) 2-(Trimethylsilyl) ethylchloroformate, Et₃N, THF;
(v) NH₂OH.HCl, CH₃CO₂Na, EtOH/H₂O, then nBu₄NBr, BrCH₂CO₂Me, 10% NaOH, toluene;
(vi) TBAF;
(vii) TsCl, Et₃N, CH₂Cl₂;
(viii) NaN₃, DMF, Δ;
(ix) H₂, Lindlar catalyst;
(x) NaN₃, NH₄Cl, CMF, Δ;
(xi) β.PhCH₂Br, Cs₂CO₃, DMF;
(xii) LiOH, Aq THF;
(xiii) CH₃NHOCH₃.HCl, isobutylchloroformate, N-methyl morpholine, THF;
(xiv) LAH, THF;
(xv) Ph₃P=CH—CH=CH—CO₂CH₃, THF;
(xvi) NaH, ICH₂CO₂CH₃, TMEDA, THF;
(xvii) 10% Pd/C, H₂.HCl/EtOH.

Scheme V below shows the synthesis of compounds further illustrating preferred examples of $R^3$ and $R^4$ of formula I.

Key intermediate (2) may be converted into the O-ether-linked side chain carboxylic acid (54) by condensation with the amine (50 of Scheme IV) as described above, with subsequent hydrolysis.

Compound (65) with an α-pentanoic acid side chain may be prepared by hydrogenation followed by hydrolysis of the unsaturated ester (64) which is prepared by condensation of flexible acid (2) with amine (47 of Scheme IV).

The glycyl derivative (56) may be prepared by condensation of the benzyl ester of glycine with the acid (55) followed by catalytic hydrogenation to remove the benzyl group. The acid (55) in turn may be prepared from the flexible acid (2) by condensation with the amine (52 of Scheme IV).

The oxime ether carboxylic acid (57) may be also prepared from the flexible acid intermediate (2) by condensation with intermediate (40) (Scheme IV) followed by hydrolysis of the ethyl ester with aqueous lithium hydroxide in THF.

The tetrazole (62) may be prepared by condensation of the amine (60) with the benzylated tetrazole carboxylic acid (44 of Scheme IV) followed by removal of the benzyl group by catalytic hydrogenation.

The intermediate amine (60) may be prepared from the flexible acid (2) by condensation of the amine (42) of Scheme IV followed by removal of the benzyloxycarbonyl group by catalytic hydrogenation.

The $\alpha$-glycinate derivative (59) may be prepared by condensation of the $\alpha$-acetic acid derivative (58) with ethylglycinate followed by hydrolysis of the ethyl ester with 1M NaOH in ethanol.

The acid (58) may be prepared from the key intermediate (2) by condensation with (37) of Scheme IV (wherein $R^1$ is methyl and Ar is phenyl) followed by hydrolysis of the methyl ester with aqueous lithium hydroxide in THF.

The $\alpha$-acetic acid (53) may be prepared from the key acid (2) by condensation with (39) of Scheme IV (wherein $R^1$ is 2-(trimethylsilyl)ethyl and Ar is p-iodophenyl) followed by removal of the 2-(trimethylsilyl)ethyl protecting group with tetrabutyl ammonium fluoride in THF.

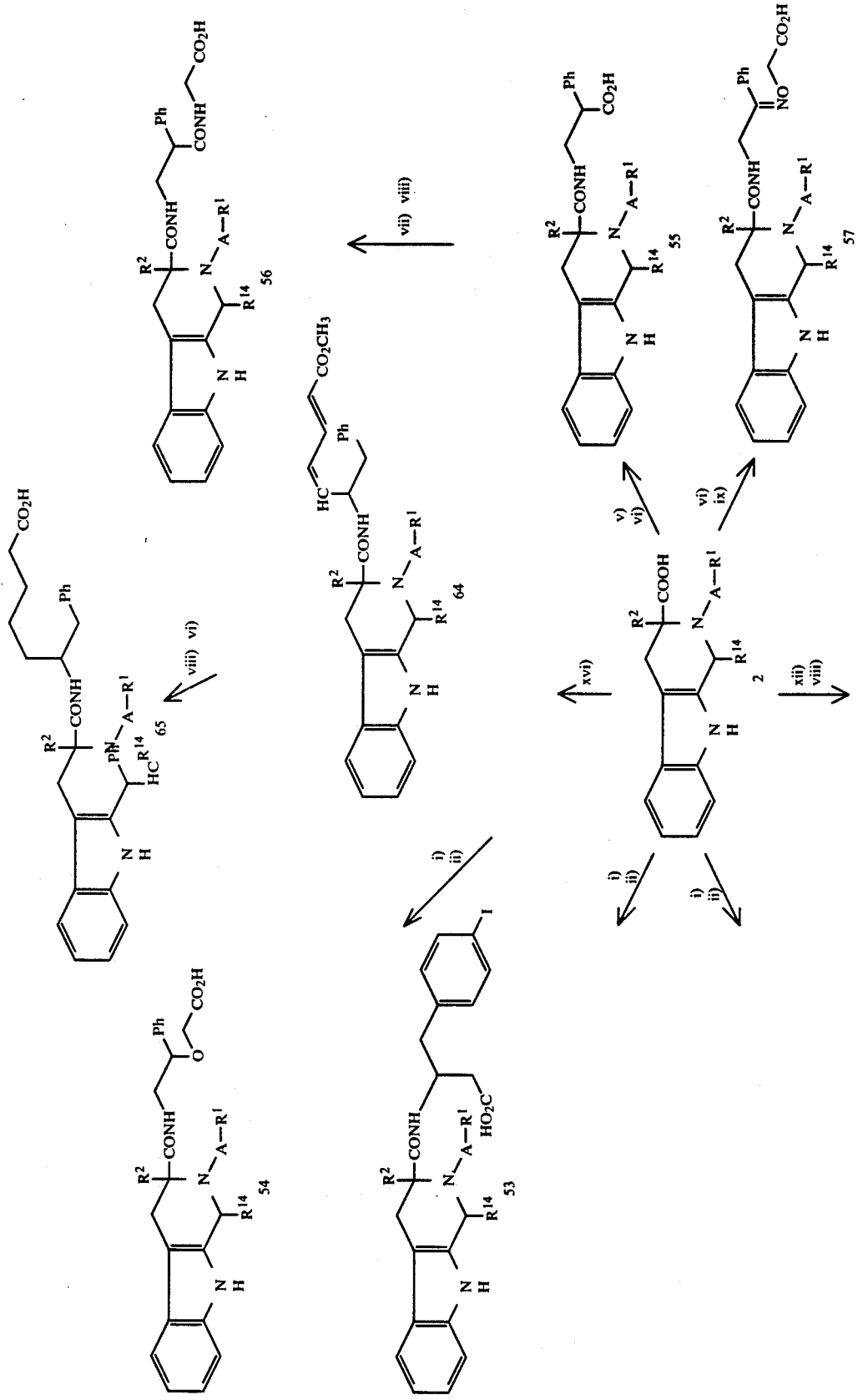

-continued
SCHEME V

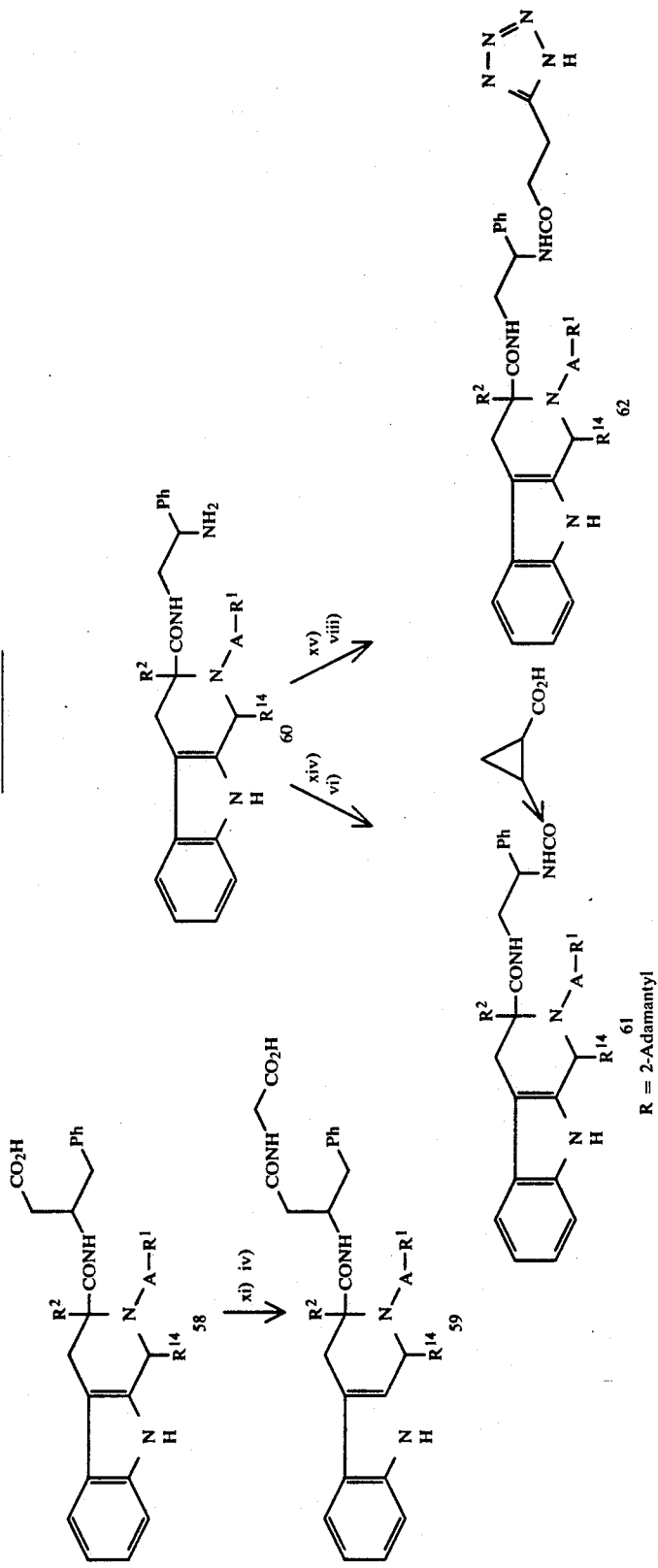

R = 2-Adamantyl

KEY
(i) DCC, HOBt, 37, EtOAc;
(ii) TBAF, THF;
(iii) DCC, HOBt, 50, NEt₃, EtOAc;
(iv) 1M NaOH, EtOH;
(v) DCC, HOBt, 52, NEt₃, EtOAc;
(vi) LiOH, aq THF;
(vii) DCC, HOBt, HCL.NH₂CH₂CO₂Bn, NEt₃, EtOAc;
(viii) 20% Pd(OH)₂/C, H₂ EtOH;
(ix) DCC, HOBt, 40, EtOAc;
(x) DCC, HOBt, 37, NEt₃, EtOAc;
(xi) DCC, HOBt, HCL.H₂NCH₂CO₂Et, NEt₃, EtOAc;
(xii) DCC, HOBt, 42, EtOAc;
(xiii) DCC, PFP, 44, EtOAc;
(xiv) DCC, HOBt, mono methyl cyclopropanedicarboxylate, EtOAc;
(xv) DCC, HOBt, 47 NEt₃, EtOAc.

Scheme VI below illustrates the synthesis of a difunctionalized derivative of formula I when $R^3$ is hydroxymethylene and $R^4$ is hydroxyl. Intermediate (2) is condensed with L-(+)-threo-2-amino-1-phenyl-1,3-propandiol using the PFP ester of (2).

SCHEME VI

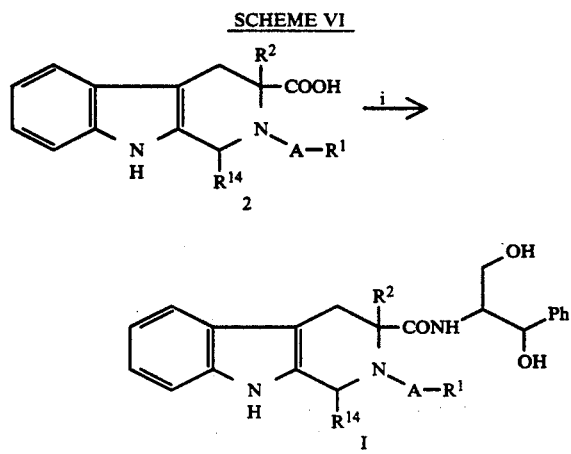

Reagents: (i) PFP, DCC, L-(+)threo-2-amino-1-phenyl-1,3-propanediol, EtOAc.

The biological activity of compounds of the present invention was evaluated employing an initial screening test which rapidly and accurately measured the binding of the tested compound to known CCK receptor sites. Specific CCK receptors have been shown to exist in the central nervous system. (See Hays et al, Neuropeptides 1:53-62, 1980; and Satuer et al, Science, 208:1155-1156, 1980.

In this screening test, the cerebral cortices taken from male CFLP mice weighing between 30-40 g were dissected on ice, weighed, and homogenized in 10 volumes of 50 mM Tris-HCl buffer (pH 7.4 at 0°-4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM MgCl$_2$, 1 nM EDTA, 5 mg/mL bovine albumin, and bacitracin (0.25 mg/mL).

In saturation studies, cerebral cortical membranes were incubated at 23° C. for 120 minutes in a final volume of 500 μliter of Hepes incubation buffer (pH 7.2) together with 0.2-20 nM tritiated-pentagastrin (Amersham International, England).

In the displacement experiments, membranes were incubated with a single concentration (2 nM) of ligand, together with increasing concentrations ($10^{-11}$ to $10^{-14}$ M) of competitive test compound. In each case, the nonspecific binding was defined as that persisting in the presence of the unlabeled octapeptide CCK$_{26-33}$ ($10^{-6}$M).

Following incubation, radioactivity bound to membranes was separated from that free in solution by rapid filtration through Whatman GF/B filters and washed three times with 4 mL of ice cold Tris-HCl buffer. Filters from samples incubated with tritiated-pentagastrin were placed in polyethylene vials with 4 mL of scintillation cocktail, and the radioactivity was estimated by liquid scintillation spectrometry (efficiency 47% to 52%).

The specific binding to CCK receptor sites was defined as the total bound tritiated-pentagastrin minus the amount of tritiated-pentagastrin bound in the presence of $10^{-6}$ octapeptide, CCK$_{26-33}$.

Saturation curves for specific tritiated-pentagastrin binding to mouse cortical membranes were analyzed by the methods of Scatchard (Ann. New York Acad. Sci. 51:660 672, 1949, and Hill (J. Physiol. 40:IV-VIII, 1910, to provide estimates for the maximum number of binding sites (B$_{max}$) and the equilibrium dissociation constant (K$_a$).

In displacement experiments, inhibition curves were analyzed by either logit-log plots or the iterative curve fitting computer program ALLFIT (DeLean, Munson and Redbard, 1978) to provide estimates of the IC$_{50}$ and nH (apparent Hill coefficient) values. (IC$_{50}$ values were defined as the concentration of test compound required to produce 50% inhibition of specific binding.)

The inhibition constant (K$_i$) of the test compound was then calculated according to the Cheng-Prusoff equation:

$$K_i = \frac{IC_{50}}{1 + [L]/K_a}$$

where [L] is the concentration of radiolabel and K$_a$ is the equilibrium dissociation constant.

The K$_i$ values for several representative compounds of the present invention are present in Table II.

TABLE II

| | Binding to CCK Receptors | |
|---|---|---|
| | Binding to Central CCK Receptors | |
| Example No. | K$_i$ (nM) | (n)$^a$ |
| 1 | 150 | 2 |
| 2 | 600 | 2 |
| 3 | IA | 2 |
| 4 | 500 | 2 |
| 5 | 730 | 2 |
| 6 | 1500 | 2 |
| 7 | 860 | 2 |
| 8 | 3000 | 2 |
| 9 | 500 | 2 |
| 10 | | |
| 11 | 3000 | 2 |
| 12 | 710 | 2 |
| 13 | 1000 | 2 |
| 14 | 1000 | 2 |
| 15 | 710 | 2 |
| 16 | 305 | 2 |
| 17 | 990 | 2 |
| 18 | 6000 | 2 |
| 19 | IA | 2 |
| 20 | | |
| 21 | | |
| 22 | | |

(n)$^a$ = Number of assays

The Ki (m) values for the CCK-B receptor are shown for representative compounds of the invention in Table III below.

Compounds of the present invention are useful as appetite suppressants as based on the tests described hereinbelow.

TABLE III

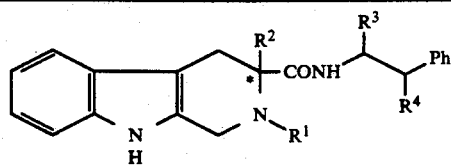

| Example | Configuration of C-3* | R¹ | R² | R³ | R⁴ | Ki (M)/CCK-B |
|---|---|---|---|---|---|---|
| 1 | R,S | 2-Adoc | Me | H | H | $1.5 \times 10^{-7}$ <br> $(4.5 \times 10^{-8})$* |
| 2 | R | 2-Adoc | Me | H | H | $6.0 \times 10^{-7}$ |
| 3 | S | 2-Adoc | Me | H | H | iA |
| 4 | R,S | 2-Adoc | Me | $CH_2OH$ | H | $5.0 \times 10^{-7}$ |
| 5 | R | 2-Adoc | Me | $CH_2OH$ | H | $7.3 \times 10^{-7}$ |
| 6 | S | 2-Adoc | Me | $CH_2OH$ | H | $1.5 \times 10^{-6}$ |
| 7 | R,S | 2-Adoc | Me | $CH_2OH$ | OH | $8.6 \times 10^{-7}$ |
| 8 | R,S | 2-Adoc | Me | H | $NH_2$ | $3.0 \times 10^{-6}$ |
| 9 | R,S | 2-Adoc | Me | H | $NHCOCH_2CH_2CO_2H$ | $5.0 \times 10^{-7}$ |
| 10 | S | 2-Adoc | Me | H | $NHCOCH_2CH_2CO_2H$ | |
| 11 | R,S | 2-Adoc | Me | H | $NHCOCH_2CH_2-CO_2CH_2Ph$ | $3.0 \times 10^{-6}$ |
| 12 | R,S | 2-Adoc | Me | H | OH | $7.1 \times 10^{-7}$ |
| 13 | R,S | 2-Adoc | Me | H | $OCOCH_2CH_2CO_2H$ | $1.0 \times 10^{-6}$ |
| 14 | R,S | 2-Adoc | Me | H | $NHCOCH_2CO_2H$ | $1.0 \times 10^{-6}$ |
| 15 | R,S | 2-Adoc | Me | H | cis $NHCOCH=CHCO_2H$ | $7.1 \times 10^{-7}$ |
| 16 | R,S | 2-Adoc | Me | $CH_2NHCOCH_2CH_2CO_2H$ | H | $3.05 \times 10^{-7}$ |
| 17 | R,S | 2-Adoc | H | H | H | $9.9 \times 10^{-7}$ |
| 18 | R,S | 2-BOC | H | COOH | H | $6.0 \times 10^{-6}$ |
| 19 | R,S | $SO_2NH$-2-Adam | Me | H | H | iA |
| 20 | R,S | 2-Adoc | Me | $CH_2COOH$ | H | |
| 21 | R,S | 2-Adoc | Me | H | 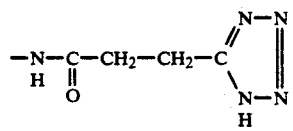 | |
| 22 | R,S | 2-Adoc | Me | H | 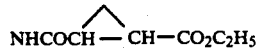 | |

In the Palatable Diet Feeding assay, adult male Hooded Lister rats weighing between 200 to 400 g are housed individually and trained to eat a palatable diet. This diet consists of Nestles sweetened condensed milk, powdered rat food, and rat water which when blended together set to a firm consistency. Each rat is presented to 20 to 30 g of the palatable diet for 30 minutes per day during the light phase of the light-dark cycle over a training period of 5 days. The intake of palatable diet is measured by weighing the food container before and after the 30-minute access period (limits of accuracy 0.1 g). Care is taken to collect and correct for any spillage of the diet. Rats have free access to pellet food and water except during the 30-minute test period.

After the training period, dose-response curves are constructed for CCK8 and several representative compounds of the present invention (n=8-10 rats per dose level). MPE₅₀ values (±95% confidence limites) are obtained for the anorectic effects of these compounds.

In therapeutic use as appetite suppression agents, the compounds of the instant invention are administered to the patient at dosage levels of from about 200 to about 2800 mg per day.

Male Hooded Lister rats (175 to 250 g) are housed individually and fasted overnight (free access to water). They are anesthetized with urethane (1.5 g/kg IP) and the trachea cannulated to aid spontaneous respiration. The stomach is perfused continuously using a modification of the original method of Ghosh & Schild in "Continuous recording of acid secretion in the rat", Br. J. Pharmac. 13:54–61, 1956 as described by Parsons in "Quantitative studies of drug-induced gastric acid secretion". (Ph.D. Thesis, University of London, 1969). The cavity of the stomach is perfused at a rate of 3 mL/min with 5.4% w/v glucose solution through both the esophageal and body cannula. The fluid is propelled by a roller pump (Gilson, Minipuls 2), through heating coils to bring its temperature to 37°±1° C. The perfusion fluid is collected by the fundic collecting funnel and passed to a pH electrode connected to a Jenway pH meter (PHM6). An output is taken from the pH meter to a Rikadenki chart recorder for the on-line recording of the pH of the gastric perfusate.

Pentagastrin is stored as a frozen aliquot and diluted to the required concentrations with sterile 0.9% w/v NaCl. Novel compounds are dissolved in sterile 0.9% w/v NaCl on the day of the experiment. Drugs are administered IV through a cannulated jugular vein as a bolus in a dose volume of 1 mL/kg washed in with 0.15 mL 0.9% w/v NaCl. Basal pH is allowed to stabilize before administration of compounds is begun. Typically 30 minutes elapses between surgery and the first compound administration.

Compounds of the invention can or may antagonize the stimulation of gastric acid secretion produced by a standard dose of 1 nmole/kg pentagastrin. The antagonism is reversible with full recovery of the response to pentagastrin.

The compounds of the instant invention are also useful as antiulcer agents as discussed hereinbelow.

Aspirin-induced gastric damage is assessed in groups of 10 rats each.

All animals are fasted for 24 hours before and throughout the experiment. Drug or vehicle is given 10 minutes before an oral dose of 1 mL of a 45-mg/mL suspension of aspirin in 0.5% carboxymethylcellulose (CMC).

The animals are sacrificed 5 hours after aspirin administration and the stomachs removed and opened for examination.

| Gastric damage is scored as follows: | |
| --- | --- |
| Score | |
| 1 | Small hemorrhage |
| 2 | Large hemorrhage |
| 3 | Small ulcer |
| 4 | Large ulcer |
| 5 | Perforated ulcer |

The mean ulcer score in the saline control group is 12.1±6.85 (±SD). Treatment with ranitidine (15 mg/kg PO) inhibits ulcer formation by 74% giving an ulcer score of 3.2±2.35 (p <0.001 compared with controls).

The specific dosages employed, however, may be varied depending upon the patient, the severity of the condition being treated, and the activity of the compound employed. Determination of optimum dosages is within the skill of the art.

The compounds of the instant invention are also useful as anxiolytic agents as described and discussed below.

Anxiolytic activity is assessed in the light/dark exploration test in the mouse (B. J. Jones, et al, Br. J. Pharmacol. 93:985-993, 1988).

The number of mice is 5 and the pretreatment time is 40 minutes.

The apparatus is an open-topped box, 45 cm long, 27 cm wide, and 27 cm high, divided into a small (2/5) area and a large (3/5) area by a partition that extended 20 cm above the walls. There is a 7.5×7.5 cm opening in the partition at floor level. The small compartment is painted black and the large compartment white. The floor of each compartment is marked into 9 cm squares. The white compartment is illuminated by a 100-watt tungsten bulb 17 cm above the box and the black compartment by a similarly placed 60-watt red bulb. The laboratory is illuminated with red light.

All tests were performed between 13 hundred hours, 0 minutes and 18 hundred hours, 0 minutes. Each mouse is tested by placing it in the center of the white area and allowing it to explore the novel environment for 5 minutes. Its behavior is recorded on videotape and the behavioral analysis performed subsequently from the recording. Five parameters are measured: the latency to entry into the dark compartment, the time spent in each area, the number of transitions between compartments, the number of lines crossed in each compartment, and the number of rears in each compartment.

In this test an increase in the time spent in the light area is a sensitive measure of, that is directly related to, the anxiolytic effects of several standard anxiolytic drugs. Drugs are dissolved in water or saline and administered either subcutaneously, intraperitoneally, or by mouth (PO) via a stomach needle.

Compounds of the invention are expected to be active by the subcutaneous route. Control animals show 3% crossings into the dark area over 5-minute measurement periods. Mice treated with a compound of the invention are expected to show more crossings into the light area and fewer crossings into the dark area, a significant (p<0.01) difference from the control anxious mice.

The compounds of the instant invention are useful as antipsychotic agents. Compounds are tested for their ability to reduce the effects of intra-accumbens amphetamine in the rat as described hereinafter.

Male Sprague Dawley (CD) Bradford strain rats are used. The rats are housed in groups of five at a temperature of 21°±2° C. on a 12 hour light-dark cycle of lights-on between 07 hours 00 minutes and 20 hours 00 minutes. Rats are fed CRM diet (Labsure) and allowed water ad libitum.

Rats are anesthetized with chloral hydrate (400 mg/kg SC) and placed in a Kopf stereotaxic frame. Chronically indwelling guide cannulae (constructed of stainless steel tubing 0.65 mm diameter held bilaterally in Parspex holders) are implanted using standard stereotaxic techniques to terminate 3.5 mm above the center of the nucleus accumbens (Ant. 0.4, Vert. 0.0, Lat. 1.6) or 5.0 mm above the central nucleus of the amygdala (Ant. 5.8, Vet. −1.8, Lat. ±4.5) (Atlas of De Groot, 1959). The guides are kept patent during a 14-day recovery period using stainless steel stylets, 0.3 mm diameter, which extend 0.5 mm beyond the guide tips.

Rats are manually restrained and the stylets removed. Intracerebral injection cannulae, 0.3 mm diameter, are inserted and drugs delivered in a volume of 0.5 $\mu$L over 5 seconds (a further 55 seconds was allowed for deposition) from Hamilton syringes attached via polythene tubing to the injection units. Animals are used on a single occasion only.

Behavioral experiments are conducted between 07 hours 30 minutes and 21 hours 30 minutes in a quiet room maintained at 22°±2° C. Rats are taken from the holding room and allowed 1 hour to adapt to the new environment. Locomotor activity is assessed in individual screened Parspex cages (25×15×15 cm (high)) (banked in groups of 30) each fitted with one photocell unit along the longer axis 3.5 cm from the side; this position has been found to minimize spurious activity counts due to, for example, preening and head movements when the animal is stationary. Interruptions of the light beam are recorded every 5 minutes. At this time animals are also observed for the presence of any nonspecific change in locomotor activity, e.g., sedation, prostration, stereotyped movements, that could interfere with the recording of locomotor activity.

The abilities of the compounds of the invention to inhibit the hyperactivity caused by the injection of amphetamine into the nucleus accumbens of the rat is measured.

An increase in locomotor activity followed the bilateral injection of amphetamine (20 $\mu$g) into the nucleus accumbens; peak hyperactivity (50 to 60 counts 5 minutes$^{-1}$) occurs 20 to 40 minutes after injection.

Intraperitoneal injection of the rats with a compound of the invention is expected to reduce the hyperactivity caused by the intra accumbens injection of amphetamine. This test is known to be predictive of antipsychotic activity (Costall, Domeney & Naylor & Tyers, Brit. J. Pharmac. 92:881-894).

The compounds of the instant invention may prevent and treat the withdrawal response produced when chronic treatment by a drug is stopped or when alcohol abuse is stopped. These compounds are therefore useful as therapeutic agents in the treatment of chronic drug or alcohol abuse as discussed and described below.

These effects of the compounds of the instant invention are illustrated, for example, in the mouse "light-/dark box" test.

Five animals are given nicotine, 0.1 mg/kg, IP BD for 14 days. After a 24-hour withdrawal period, a compound of the invention is given. The increased time spent in the light area is a sensitive measure of the effect of the compound as an agent to treat withdrawal effects from nicotine.

Five mice are given diazepam, at 10 mg/kg IP BD for 7 days. Withdrawal is for a 24-hour period; the compound is given. The increased time spent in the light section shows the effect of the compound.

The long-term treatment and withdrawal from alcohol is listed by five mice given alcohol in drinking water 8% w/v for 14 days. After a withdrawal period of 24 hours, a compound of the invention is given. The amount of time spent in the light section after the compound is administered demonstrates the effectiveness of the compound.

To illustrate the effectiveness in the long-term treatment and withdrawal from cocaine, five mice are given cocaine as 1.0 mg/kg IP BD for 14 days. The increased time in the light section illustrates the effectiveness of the compound in the treatment.

The anxiolytic effects of compounds of the invention are shown by the Rat Social Interaction Test when paired rats are dosed SC. The anxiolytic effect of the compounds is indicated by the increase in time spent in social interaction compared with the control value C. (Costall, B., University of Bradford).

The anxiolytic effects of a compound of the invention are shown by the Rat Elevated X-Maze Test. The anxiolytic effect is indicated by the time spent in the open arm end section compared with control C.

A compound of the invention is expected to depress the flexor response in a stimulated spinalized decerebrated rat preparation similar to morphine. The effect of giving a compound with morphine greatly potentiates the effect, which lasts for 3 hours.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5 to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Preferred pharmaceutically acceptable salts are benzathine, chloroprocaine, choline, diethanolamine, ethylenediamine, meglumine (N-methylglucamine), procaine, aluminum, calcium, lithium, magnesium, potassium, sodium, zinc, diethylamine and tromethamine.

Especially preferred pharmaceutically acceptable salts are N-methylglucamine and sodium.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The following examples illustrate particular methods for preparing compounds in accordance with this invention. These examples are illustrative and are not to be read as limiting the scope of the invention as it is defined by the appended claims.

EXAMPLE 1

($\pm$)1,3,4,9-Tetrahydro-3-methyl-3-[[2-phenylethyl)amino]carbonyl]-2H-pyrido[3,4-b]indole-2-carboxylic acid,tricyclo[3.3.1.1$^{3,7}$]dec-2-yl ester

Step 1

D,L-alpha-Methyl-tryptophane methyl ester (20.0 g, 86 mmol) was dissolved in a warm mixture of methanol (75 mL) and water (75 mL), treated with 37% formalin solution in water (8.0 g) and heated to reflux over 16 hours. The reaction mixture was cooled to room temperature and diluted with ethyl acetate (300 mL). The organic layer was separated, washed with water, dried over Na$_2$SO$_4$ and evaporated in vacuo. After treating the residue with ethyl acetate [(3-methyl)9H-1,2,3,4-tetrahydro-$\beta$-carboline-3-yl]carboxylic acid methyl ester (12.75 g, 60.7%) was isolated as a white solid.

Step 2

To a stirred solution of [(3-methyl)-9H-1,2,3,4-tetrahydro-β-carboline-3-yl]-carboxylic acid methyl ester (10.0 g, 41 mmol) in THF (10 mL) was added 2-adamantyl chloroformate (8.8. g, 41 mmol) and the solution was treated with diisopropyl ethylamine (5.3 g, 41 mmol) in THF (150 mL). The reaction mixture was stirred for 4 hours at room temperature, evaporated in vacuo and partitioned between ethyl acetate (100 mL) and water (50 mL). The organic layer was separated, washed successively with 7.5% citric acid solution (50 mL), 8% NaHCO3 solution (50 mL) and then dried over Na2SO4. The solvent was evaporated in vacuo and the residue was treated with n-pentane. [(2N-Adamantyloxycarbonyl-3-methyl)-9H-1,2,3,4-tetrahydro-β-carboline-3-yl]-carboxylic acid methylester (13.5 g, 81.8%) was separated by filtration.

Step 3

To a solution of [(2N-Adamantyloxycarbonyl-3-methyl)-9H-1,2,3,4-tetrahydro-β-carboline-3-yl]-carboxylic acid methyl ester (17.1 g, 40 mmol) in ethanol (150 mL) was added KOH (9.2 g, 160 mmol). The reaction mixture was heated to reflux over 16 hours then cooled to room temperature and poured into water (400 mL). After extraction with dichloromethane (3 times with 100 mL) the combined organic phases were dried over Na2SO4 and evaporated in vacuo. The crude material was treated with ether and [(2N-adamantyloxycarbonyl-3-methyl)-9H-1,2,3,4-tetrahydro-β-carboline-3-yl]-carboxylic acid (13.5 g, 81.8%) was separated by filtration.

Step 4

To a solution of [(2N-Adamantyloxycarbonyl-3-methyl)-9H-1,2,3,4-tetrahydro-β-carboline-3-yl]-carboxylic acid (0.41 g, 1 mmol) in anhydrous THF (10 mL) was added N,N'-carbonyldiimidazole (0.16 g, 1 mmol) and the reaction mixture stirred at room temperature for 2 hours. To this was added phenylethylamine (0.12 g, 1 mmol) and the reaction mixture stirred for another 3 hours at room temperature. The mixture was evaporated in vacuo and the residue chromatographed on silica gel using ethyl acetate:cyclohexane (90:10%) as eluant to give the title compound (60 mg). mp: 155°–117° C.

EXAMPLE 2

(R)-1,3,4,9-Tetrahydro-3-methyl-3-[[2-phenylethyl)amino]carbonyl]-2H-pyrido[3,4-b]indole-2-carboxylic acid, tricyclo[3.3.1.1³,⁷]dec-2-yl ester Method was as described for Example 1, step 1 to step 4, but using D-alpha-methyl-tryptophane methyl ester as starting material to synthesize the R-enantiomer 2 as a light yellow solid (48 mg, 51.6%). $[\alpha]_D^{RT} = +13.6°$ (c=0.25/MeOH). mp: 86°–94° C.

EXAMPLE 3

(S)-1,3,4,9-Tetrahydro-3-methyl-3-[[2-phenylethyl)amino]carbonyl]-2H-pyrido[3,4-b]indole-2-carboxylic acid, tricyclo[3.3.1.1³,⁷]dec-2-yl ester Method was as described for Example 1, step 1 to step 4, but using L-alpha-methyl-tryptophane methyl ester as starting material to synthesize the S-enantiomer 3 as a light beige solid from pentane (870 mg, 48.6%). $[\alpha]_D^{RT} = -10.4°$ (c=0.528/MeOH). mp: 110°–118° C.

EXAMPLE 4

1,3,4,9-Tetrahydro-3-[[[1-(hydroxymethyl)-2-phenylethyl]amino]carbonyl]-3-methyl-2H-pyrido[3,4-b]indole-2-carboxylic acid,tricyclo[3.3.1.1³,⁷]dec-2-yl ester
(mixture of diastereomers)

To a solution of [(2N-Adamantyloxycarbonyl-3-methyl)-9H-1,2,3,4-tetrahydro-β-carboline-3-yl]-carboxylic acid (0.27 g, 0.7 mmol) from Example 1, step 4, in dry THF (15 mL) at −10° C. was added with stirring N-methylmorpholine (67 mg, 0.7 mmol) and isobutyl chloroformate (80 mg, 0.7 mmol). After stirring for another hour at that temperature (S)-(−)-2-amino-3-phenyl-1-propanol was added and the reaction mixture was stirred overnight at room temperature. The mixture was evaporated in vacuo, the residue was dissolved in ethyl acetate and washed successively with 7.5% citric acid solution and NaHCO3 solution. The organic layer was dried over Na2SO4, evaporated in vacuo and the residue was purified by chromatography on silica gel using ethyl acetate as eluant to give the title compound (150 mg, 33.3%). mp: 88°–91° C.

EXAMPLE 5

(R) 1,3,4,9-Tetrahydro-3-[[1-(hydroxymethyl)-2-phenylethyl]amino]carbonyl]-3-methyl-2H-pyrido[3,4-b]-indole-2-carboxylic acid,tricyclo[3.3.1.1³,⁷]dec-2-yl ester To a solution of(R)-[(2N-Adamantyloxycarbonyl-3-methyl)-9H-1,2,3,4-tetrahydro-β-carboline-3-yl]-carboxylic acid, as described in Example 2, (305 mg, 0.75 mmol) in ethyl acetate (4 mL) was added successively pentafluorophenol (140 mg, 0.75 mmol), N,N'-dicyclohexylcarbodiimide (155 mg, 0.75 mmol) and 1-hydroxybenzotriazole hydrate (10 mg). After 1 hour with stirring (S)-(−)-2-amino-3-phenyl-1-propanol (114 mg, 0.75 mmol) was added and the reaction mixture stirred for another 70 hours at room temperature. The reaction mixture was diluted with ethyl acetate (50 mL) and successively washed with 7.5% citric acid solution, and water. The organic layer was dried over Na2SO4, evaporated in vacuo and the residue chromatographed on silica gel using toluene/ethanol (99–98.5:1–1.5%) as eluant to isolate the title compound as a light beige solid from toluene (110 mg, 27.1%). $[\alpha]_D^{RT} = -10.9°$ (c=0.052/MeOH). mp: 106°–113° C.

EXAMPLE 6

(S)-1,3,4,9-Tetrahydro-3-[[[1-(hydroxymethyl)-2-phenylethyl]amino]carbonyl]-3-methyl-2H-pyrido[3,4-b]indole-2-carboxylic acid,tricyclo[3.3.1.1³,⁷]dec-2-yl ester ester Method was as described for Example 5 but using (S)-[(2N-Adamantyloxycarbonyl-3-methyl)-9H-1,2,3,4-tetrahydro-β-carboline-3-yl]-carboxylic acid, as described in Example 3. The crude residue was chromatographed on silica gel using toluene/ethanol (99.75–98:0.25–2%) as eluant to yield the title compound as a white solid from toluene/n-hexane (505 mg, 31.1%). $[\alpha]_D^{RT} = -40.8°$ (c=0.510/MeOH). mp: 178°–182° C.

EXAMPLE 7

1,3,4,9-Tetrahydro-3-[[[1-(hydroxymethyl)-2-hydroxy-2-phenylethyl]amino]carbonyl]-3-methyl-2H-pyrido[3,4-b]-indole-2-carboxylic acid,tricyclo[3.3.1.1$^{3,7}$]dec-2-yl ester The title compound was prepared by the same method as Example 5 except that (R,S)-[(2N-Adamantyloxycarbonyl-3-methyl)-9H-1,2,3,4-tetrahydro-β-carboline- 3-yl]-carboxylic acid (408 mg, 1 mmol) prepared in Example 1, step 4, and (1S,2S)-(+)-2-amino-1-phenyl-1,3-propanediol (334 mg, 1 mmol) was used. The crude residue was chromatographed on silica gel using cyclohexane/ethyl acetate (90:10%) as eluant to isolate the title compound as a pale yellow solid from n-pentane (220 mg, 39.5%). mp. 141°-148° C.

EXAMPLE 8

3-[[(2-Amino-2-phenylethyl)amino]carbonyl]-1,3,4,9-tetrahydro-3-methyl]-2H-pyrido[3,4-b]indole-2-carboxylic acid, tricyclo[3.3.1.1$^{3,7}$]dec-2-yl ester, (mixtures of diastereomers)

Step 1

To a solution of benzyloxycarbonyl-L-phenylalaninol tosylate (27.6 g, 65 mmol) in dry DMF (250 mL) was added sodium azide (4.6 g, 71 mmol) and the resulting mixture heated to 80° C. for 5 hours. This was allowed to cool and then poured into water (1 L) and the product extracted with ether. The organic extract was washed with water, dried over Na$_2$SO$_4$ and evaporated in vacuo to give the azide (14.7 g, 78.0%) as a white solid.

Step 2

A solution of the azide (14.5 g, 49 mmol) from step 1 in ethyl acetate (450 mL) was treated with Raney-Nickel (B 113W, 4.0 g) and put under an atmosphere of hydrogen at 80 bar with agitation for 16 hours at room temperature. After no more hydrogen was seen to be taken up, the mixture was filtered over celite and concentrated in vacuo to give the amino compound as a light yellow oil.

To a solution of (R,S)-[(2N-adamantyloxycarbonyl-3-methyl)-9H-1,2,3,4-tetrahydro-β-carboline-3-yl]-carboxylic acid (4.7 g, 11 mmol) in dry THF (15 mL) at −10° C. was added with stirring N-methylmorpholine (1.1 g, 11 mmol) and isobutyl chloroformate (1.3 g, 11 mmol). The reaction mixture stirred for another hour at that temperature and then overnight. The amino compound (2.8 g, 11 mmol) from step 3 in dry THF (20 mL) was added and the reaction mixture stirred for another 20 hours. The precipitate was filtered off, the filtrate was concentrated in vacuo and the residue was chromatographed on silica gel using cyclohexane:ethyl acetate (50%) as eluant to give benzyl-[(2N-adamantyloxycarbonyl-3-methyl) 9H-1,2,3,4-tetrahydro-β-carboline-3-yl]-carboxylic acid-[(1-phenyl)-ethyl]amido]carbamate (2.8 g, 38.2%) as a light yellow foam.

Step 4

A solution of benzyl-[(2N-adamantyloxycarbonyl-3-methyl)-9H-1,2,3,4-tetrahydro-β-carboline-3-yl]-carboxylic acid-[(1-phenyl)-ethyl]amido]carbamate (2.8 g, 4.2 mmol) in ethanol (60 mL) was treated with 20% palladium on carbon (0.5 g, 50% water) and put under an atmosphere of hydrogen of 80 bar at room temperature with agitation. After 3 days when no more hydrogen was seen to be taken up, the mixture was filtered over celite and concentrated in vacuo to isolate the product as a mixtures of diastereomers as a pale yellow foam from ethyl acetate (1.5 g, 98.7 %). mp: 102°-104° C.

EXAMPLE 9

3-[[[2-(3-Carboxy-1-oxopropyl)-amino]-2-phenylethyl]amino]carbonyl]-1,3,4,9-tetrahydro-3-methyl-2H-pyrido[3,4-b]indole-2-carboxylic acid, tricyclo[3.3.1.1$^{3,7}$]dec-2-yl ester, [R-(R*,R*)] and [R-(R*,S*)]-

A solution of 2H-Pyrido[3,4-b]indole-2-carboxylic acid, 1,3,4,9-tetrahydro-3-methyl-3-[[(2-amino-2-phenylethyl)amino]carbonyl],tricyclo[3.3.1.1$^{5,7}$]dec-2-yl ester (1.0 g, 1.9 mmol) in dry ethyl acetate (10 mL) was added to a mixture of succinic anhydride (0.2 g, 1.9 mmol) and DMAP (0.24 g, 1.9 mmol) in dry ethyl acetate (40 mL) and heated to reflux for 4 hours. The reaction mixture was cooled to room temperature and ethyl acetate (150 mL) was added. The solution was washed with 7.5% citric acid solution, dried over Na$_2$SO$_4$ and evaporated in vacuo. The residue was stirred with diethyl ether for 2 hours, then the product was filtered of, washed with ether and dried in vacuo to isolate the title compound (1.1 g, 92.5%) as a light tan solid. mp: 111°-113° C.

EXAMPLE 10

3-[[[2-(R)-(3-Carboxy-1-oxopropyl)amino]-2-phenylethyl]amino]carbonyl]-1,3,4,9-tetrahydro-3-(S)-methyl-2H-pyrido[3,4-b]indole-2-carboxylic acid, tricyclo[3.3.1.1$^{3,7}$]dec-2-yl ester Method was as described for Example 9, but using (S)-2H-Pyrido-[3,4-indole-2-carboxylic acid, 1,3,4,9-tetrahydro-3-methyl-3-[[(2-amino-2-phenylethyl)amino]-carbonyl],tricyclo[3.3.1.1$^{5,7}$]dec-2-yl ester, as described in Example 3, to yield the title compound as a pale beige solid from n-pentane (60 mg, 10%). $[\alpha]_D^{RT} = -41.4°$ (c=0.384/MeOH). mp: 201°-204° C.

EXAMPLE 11

3-[3-[3-[2-[2-[1,4-Dioxo-4-(phenylmethoxy)butyl]amino]-2-phenylethyl]amino]carbonyl]-1,3,4,9-tetrahydro-3-methyl]-2H-pyrido[3,4-b]indole-2-carboxylic acid, tricyclo[3.3.1.1$^{3,7}$]dec-2-yl ester (mixture of diastereomers)

Step 1

To a solution of the amino compound (6.5 g, 27 mmol) as prepared in Example 8, step 2, in dry dioxane (30 mL) was added under ice cooling di-BOC (6.5 g, 30 mmol) in dry dioxane. The reaction mixture was allowed to warm to room temperature and stirred for another 2 hours. The organic solvent was evaporated in vacuo, the residue was taken up in ethyl acetate and the solution was washed with 7.5% citric acid solution. The organic layer was dried over Na$_2$SO$_4$ and evaporated in vacuo to isolate the required 1N- benzyloxycarbonyl-2N-tert-butyloxy-carbonyl-2-(L)-phenyl-ethylene-1,2-diamine (9.1 g, 100%) as a white solid.

Step 2

A solution of 1N-benzyloxycarbonyl-2N-tert-butyloxy-carbonyl-2-(L)-phenyl-ethylene-1,2-diamine (9.0 g, 25 mmol) in ethanol (180 mL) was treated with 10% palladium on carbon (1.8 g, 50% w/w) and placed under an atmosphere of hydrogen at room temperature with agitation. After no more hydrogen was seen to be taken up the mixture was filtered over celite and concentrated in vacuo to isolate tert-butyloxycarbonyl-L-phenyl-ethylene-1,2-diamine as an oil which became a solid from n-pentane. This was filtered off and dried in the vacuo to isolate the product (4.6 g, 74.2%).

Step 3

To a solution of benzyl-hemisuccinate (3.9 g, 19 mmol) in dry THF (50 mL) was added at room temperature N,N'-carbonyldiimidazole (3.0 g, 19 mmol) and the reaction mixture stirred for 1 hour. Tert-butyloxycarbonyl-L-phenyl-ethylene-1,2-diamine (4.6 g, 19 mmol) was then added and the reaction mixture was stirred overnight at room temperature. The solution was evaporated in vacuo, the residue was dissolved in ethyl acetate and washed successively with 7.5% citric acid solution and $NaHCO_3$ solution. After drying over $Na_2SO_4$ the organic solvent was evaporated in vacuo and the residue chromatographed on silica gel using cyclohexane:ethyl acetate (50%) as eluant to isolate the required amide (4.5 g, 54.2%) as an oil.

Step 4

BOC-protected amino compound (4.4 g, 10 mmol), as prepared in step 3, was dissolved in methylene chloride and trifluoroacetic acid (10 mL) was added with stirring. The reaction mixture was stirred for another 5 hours at room temperature, evaporated in vacuo, the residue was taken up in ethyl acetate, washed with $NaHCO_3$ solution, dried over $Na_2SO_4$ and evaporated in vacuo to isolate the required amino compound (3.4 g, 100%) as a oil to be stored at $-20°$ C.

Step 5

Method was as described for Example 4, but using the amino compound prepared in step 4. The crude product was chromatographed over silica gel using cyclohexane/ethyl acetate (50%) as eluant to give the title compound (0.7 g, 26.9%) as a white solid from ether/n-pentane. mp: $59°-62°$ C.

EXAMPLE 12

3-[[(2-Hydroxy-2-phenylethyl)amino]carbonyl]-1,3,4,9-tetrahydro-3-methyl]-2H-pyrido[3,4-b]indole-2-carboxylic acid, tricyclo[3.3.1.1$^{3,7}$]dec-2-yl ester Method was as described for Example 5, but using (R,S)-[(2N-Adamantyloxycarbonyl-3-methyl)-9H-1,2,3,4-tetrahydro-β-carboline-3-yl]-carboxylic acid from Example 1, step 3, (100 mg, 0.26 mmol) and 2-amino-1-phenylethanol (100 mg, 0.73 mmol). After working up in the usual manner the product was isolated by crystallization from ethanol/n-pentane as a pale yellow solid (40 mg, 29.2%). mp: $102°-111°$ C.

EXAMPLE 13

Butanedioic acid,mono[2-[[[2,3,4,9-tetrahydro-3-methyl-2-(tricyclo[3.3.1.1$^{3,7}$]dec-2-yloxy)carbonyl]-1H-pyrido[3,4-b]indole-3-yl]carbonyl]amino]-1-phenethyl]ester Method was as described for Example 9, but using the hydroxy compound (250 mg, 0.47 mmol) from Example 12 to yield the title compound as a beige solid from n-pentane (210 mg, 70.7%). mp: $79°-84°$ C.

EXAMPLE 14

3-[[[2-[(3-Carboxyacetyl)amino]-2-phenethyl]-amino]carbonyl]-1,3,4,9-tetrahydro-3-methyl-2H-pyrido[3,4-b]indole-2-carboxylic acid, [tricyclo-[3.3.1.1$^{3,7}$]dec-2-yl ester (mixture of diastereomers)

Step 1

To a solution of the amino compound (450 mg, 0.85 mmol) from Example 8, step 4 and triethylamine (86 mg, 0.85 mmol) in THF (7 mL) was added dropwise at room temperature a solution of chloromalonic acid methyl ester in THF (5 mL). Stirring was continued overnight, then the organic solvent was evaporated in vacuo, the residue was taken up in ethyl acetate and the organic layer was washed with water. After drying the organic phase over $Na_2SO_4$ and evaporating in vacuo the residue was used for the next step without further purification.

Step 2

To an ice cooled solution of the ester (400 mg, 0.64 mmol), synthesized in the last step, in THF (15 mL) was dropped a solution of LiOH (6.4 mg, 0.64 mmol) in water (5 mL) and the reaction mixture was stirred for 4 hours at room temperature. The solvent was evaporated in vacuo and the residue was taken up in ethyl acetate and successively washed with 7.5% citric acid solution and water. The organic layer was dried over $Na_2SO_4$ and then evaporated in vacuo. The residue was stirred with ether (50 mL) filtered and the filtrate was evaporated in the vacuo to isolate the product (91 mg, 23.2%) as a beige solid. mp: $157°-161°$ C.

EXAMPLE 15

3-[[[2-[(3-Carboxy-1-oxo-2-propenyl)amino]-b 2-phenethyl]amino]carbonyl]1,3,4,9-tetrahydro-3-methyl-2H-pyrido[3,4-b]indole-2-carboxylic acid, [tricyclo-[3.3.1.1$^{3,7}$]dec-2-yl ester (mixture of diastereomers)

Method was as described for synthesis of Example 9 but using maleic acid anhydride. The crude residue was chromatographed on silica gel using ethyl acetate/cyclohexane (90:10%) to yield the title compound as a pale beige solid from methanol/ethyl acetate (122 mg, 19.6%). mp: $240°-245°$ C.

EXAMPLE 16

3-[[1-(3-Carboxy-1-oxopropyl)amino]methyl]-1-phenethyl]amino]carbonyl]-1,3,4,9-tetrahydro-3-methyl2H-pyrido[3,4-b]indole-2-carboxylic acid, [tricyclo-[3.3.1.1$^{3,7}$]dec-2 yl ester (mixture of diastereomers)

Step 1

To an ice cooled suspension of L-2-amino-3-phenyl-1-propanol in dioxane (200 mL) was dropped a solution of di-tert. butyldicarbonate in dioxane (50 mL). The reaction mixture was allowed to warm to room temperature and was stirred for another 48 hours. The organic solvent was evaporated in vacuo, the residue was dissolved in ethyl acetate and washed with 7.5% citric acid solution and water. The organic layer was dried over $Na_2SO_4$, evaporated in vacuo and the product solidified upon drying (35.12 g, 99%).

Step 2

An ice cooled solution of tert.-butyloxycarbonyl-L-phenylalaninol (25 g, 99 mmol) in pyridine (50 mL) was treated with p-toluene sulphonyl chloride (19.6 g, 99 mmol) with stirring. The mixture was left overnight at room temperature and then poured into 600 mL ice water. The solid was filtered off, washed with water, then n-hexane and dried in the vacuo to give the required tosylate (32 g, 79.4%) which was used for the next step without further purification.

Step 3

A solution of the tosylate from step 2 (30.0 g, 74 mmol) in DMF (100 mL) was treated with sodium azide (5.2 g, 80 mmol) and the reaction mixture heated to 120° C. over 2 hours. Then the solution was evaporated in vacuo, the residue was taken up in ethyl acetate and the organic layer washed three times with water, then dried over $Na_2SO_4$ and the product was isolated as an oil which was used for the next step without further purification (11.8 g).

Step 4

A solution of the compound from step 3 (4.0 g, 14.5 mmol) in dichloromethane (10 mL) was treated at room temperature with trifluoroacetic acid (10 mL). After 2 hours the reaction mixture was evaporated in vacuo and the residue was chromatographed on silica gel using ethyl acetate/cyclohexane (80:20%) and then ethyl acetate/ethanol (90:10%) as eluant to isolate the required amine as an oil (2.4 g, 78.4%).

Step 5

Method was as described for synthesis of Example 5 but using the amine from step 4 (350 mg, 2 mmol). The residue was chromatographed on silica gel using ethyl acetate/cyclohexane (50%) as eluant to isolate the pure product as a solid from diisopropylether (350 mg, 25.2%).

Step 6

A reaction mixture of the azide from step 5 (350 mg, 0.5 mmol) was treated with Raney Nickel (500 mg) and put under an atmosphere of hydrogen at 80 bar and room temperature for 12 hours with agitation. The reaction mixture was filtered and the filtrate evaporated in vacuo. The product was isolated as a solid from ether/n-pentane (170 mg, 51.5%).

Step 7

Method was as described for synthesis of Example 9 but using the amino compound from step 6. After working up in the usual manner the title compound was isolated as a pale gray solid from ethyl acetate (70 mg, 29.5%). mp: 148°–152° C.

EXAMPLE 17

(+/−)-1,3,4,9-Tetrahydro-3-[[(2-phenethyl)amino]carbonyl]-2H-pyrido[3,4-b]indole-2-carboxylic acid, [tricyclo[3.3.1.1$^{3,7}$]dec-2-yl ester

Step 1

In a mixture of water (50 mL) and methanol (150 mL) was stirred tryptophane methyl ester hydrochloride (25.5 g, 0.1 mol) and formaldehyde solution (3.0 g, 0.1 mol) and the mixture stirred at reflux for 16 hours. Then cooled to room temperature, evaporated in vacuo, partitioned between $NaHCO_3$ solution (200 mL) and dichloromethane (200 mL) and the organic layer was separated and dried over $Na_2SO_4$. After evaporating the organic phase in vacuo the product was isolated as a white solid upon drying (21.5 g, 80.5%).

Step 2

Method was as described for Example 1, step 2, but using β-carboline derivative from step 1 (2.3 g, 10.5 mmol) and 2-adamantyl chloroformate to yield the product crystallized from ether (3.35 g, 82.0%). mp: 204°–207° C.

Step 3

Method was as described for Example 1, step 3, but using β-carboline methyl ester (3.2 g, 7.8 mmol) from step 2 and KOH to synthesize β-carboline carboxylic acid as a pale beige solid from ethyl acetate/methanol (3.0 g, 100%).

Step 4

Method was as described for Example 5 but using the carboxylic acid from step 3 (1.53 g, 4 mmol) and phenethyl amine (975 mg, 8.1 mmol). The crude residue was chromatographed on silica gel using toluene/ethanol (99.5:0.5%) as eluant to give the required product as a white solid from ether (885 mg, 43.0%). mp: 198°–201° C.

EXAMPLE 18

3-[[1(I-Carboxy-2-phenethyl)amino]carbonyl]-1,3,4,9-tetrahydro-2H-pyrido[3,4-b]indole-2-carboxylic acid, 1,1-dimethylethyl ester

Step 1

The amino acid (10.8 g, 50 mmol) (J. Amer. Chem. Soc. 1959, 71, 527) was dissolved in water (100 mL) and THF (100 mL). This was treated with NaOH (4.0 g, 100 mmol) and stirred till a clear solution. To this was added diBOC (21.8 g, 100 mmol) and stirred 0.5 hours. Another amount of NaOH was added (2.0 g, 50 mmol) and the reaction mixture was stirred overnight. The organic solvent was evaporated in vacuo and the pH was adjusted to 4–5 with conc. HCl. The solution was extracted with dichloromethane, the organic layer dried over $Na_2SO_4$ and evaporated in vacuo. The residue was treated with petrol ether to isolate the product as a pale beige solid (14.0 g, 88.6 %).

Step 2

In an ice-bath was stirred the β-carboline carboxylic acid from step 1 (6.33 g, 20 mmol) in THF (75 mL) and N-methyl-morpholine (2.23 g, 22 mmol) in THF (5 mL) was added followed by isobutyl chloroformate (2.73 g, 20 mmol). This was stirred for 0.5 hours and then a solution of phenylalanine benzyl ester (5.6 g, 22 mmol) in THF (80 mL) was added. The reaction mixture was stirred for another 5 minutes at that temperature and then warmed up to room temperature. After 2.5 hours the reaction mixture was partitioned between ethyl acetate and 7.5% citric acid solution. The organic layer was separated, washed successively with $NaHCO_3$ solution and water and the organic layer was dried over $Na_2SO_4$. Evaporating in the vacuo gives an yellow oil which was Flash-chromatographed on silica gel using dichloromethane/methanol 90:10% to give the benzyl ester as a white foam (3.65 g, 30.0%).

Step 3

A solution of the benzyl ester from step 2 (7.3 g, 13.2 mmol) in methanol (75 mL) was treated with 10% palladium on carbon (1.0 g) and placed under an atmosphere of hydrogen at room temperature with agitation. After no more hydrogen was seen to be taken up the mixture was filtered and concentrated in vacuo to isolate the target molecule as a yellow foam which was recrystallized from ethanol. Yield: 5.2 g (86.7 %). mp: 109°–113° C.

EXAMPLE 19

(+/−)-1,3,4,9-Tetrahydro-3-methyl-N-(2-phenylethyl)-2-(tricyclo[(3.3.1.1$^{3,7}$]dec-2-ylamino]sulfonyl]1H-pyrido-[3,4-b]indole-3-carboxamide

Step 1

To a solution of [(3-methyl)9H-1,2,3,4- tetrahydro-β-carboline-3-yl]-carboxylic acid methyl ester (0.60 g, 2.5 mmol) in dry THF at room temperature was added 2 adamantylamino-sulfonyl chloride (0.84 g, 3 mmol) and triethylamine (0.31 g, 3 mmol) was added dropwise. The reaction mixture stirred for another 16 hours at room temperature and more 2-adamantylamino-sulfonyl chloride (0.20 g, 0.7 mmol) and triethylamine (72 mg, 0.7 mmol) was added. The reaction was evaporated after 24 hours, the residue was dissolved in ethyl acetate and washed successively with 7.5% citric acid solution and NaHCO$_3$ solution. The organic layer dried over Na$_2$SO$_4$ and evaporated in vacuo. The residue was chromatographed on silica gel using ethyl acetate: cyclohexane (50%) as eluant to yield D,L-[2N-(Adamantylamino)sulfonyl-3-methyl-9H-1,2,3,4-tetrahydro-β-carboline-3-yl]-carboxylic acid methyl ester. (0.5 g, 45.5%).

Step 2

A solution of the ester (500 mg, 1 mmol) from step 1 in dioxane/water 1:1 (20 mL) was treated at room temperature with LiOH (120 mg, 3 mmol) and stirred for three hours. The organic solvent was evaporated in vacuo, the residue was partitioned between ethyl acetate and water, the organic layer was separated, washed with 7.5% citric acid solution and dried over Na$_2$SO$_4$. After evaporating the organic solvent in vacuo the acid (400 mg, 82.5%) was isolated as a solid upon drying.

Step 3

Method was as described for Example 7 but using D,L [2N-(adamantylamino)sulfonyl-3-methyl-9H-1,2,3,4-tetrahydro-β-carboline-3-yl]-carboxylic acid (0.20 g, 0.43 mmol) and 2 phenylethylamine (0.53 g, 0.43 mmol). The crude residue was chromatographed on silica gel using ethyl acetate: cyclohexane (90:10%) as eluant to obtain the title compound (0.15 g, 62.8%) as a solid from ether/n-pentane. mp: 55°–58° C.

EXAMPLE 20

3-[[[3-Carboxy-1-(phenylmethyl)propyl]amino]carbonyl]-1,3,4,9-tetrahydro-3-methyl-2H-pyrido[3,4-b]indole-2-carboxylic acid, tricyclo[3.3.1.1$^{3,7}$]dec-2-yl ester

Step 1

To a stirred solution of N-t-butyloxycarbonyl-S-phenylalanine (7.1 g, 26.8 mmol) in THF (50 mL) at −10° C. was added dropwise isobutyl-chloroformate (3.4 mL, 26.8 mmol). After 20 minutes the reaction mixture was filtered and a solution of diazomethane (40 mmol) in ether (80 mL) was added in one portion to the filtrate at −10° C. with stirring. The cooled solution stirred for another 30 minutes at that temperature and then for 16 hours at room temperature. The reaction mixture was diluted with ether (100 mL) and successively washed with 7.5% citric acid solution, water, NaHCO$_3$ solution and water again. The organic layer was dried over Na$_2$SO$_4$ and evaporated in vacuo to yield the diazoketone as a yellow oil (8.0 g, 100%).

Step 2

To a stirred solution of the diazoketone (7.0 g, 24 mmol) from step 1 in methanol (70 mL) was added a solution of silver(I)benzoate (1.37 g, 6 mmol) in triethylamine (14 mL). When nitrogen evolution has ceased a further portion of silver(I)benzoate solution (0.3 mL) was added and the solution was stirred for another 15 minutes. The reaction mixture was treated with charcoal, filtered and evaporated in vacuo. The residue was taken up in ethyl acetate and successively washed with water, NaHCO$_3$ solution, 1M HCl, NaHCO$_3$ solution and brine. The organic phase was dried over Na$_2$SO$_4$ and evaporated in vacuo to give the methyl ester as an oil (6.0 g, 85%).

Step 3

To a stirred solution of methyl-3-(t-butyloxycarbonylamino)-4-phenylbutyrate (2.0 g, 7mmol) from step 2 in dichloromethane (5 mL) was added trifluoroacetic acid (5 mL). After stirring for 3 hours at room temperature the solvents were evaporated in vacuo and the residue was dissolved in ethyl acetate. The organic layer was washed with NaHCO$_3$ solution and water, dried over Na$_2$SO$_4$ and evaporated in vacuo to give the desired amine (600 mg, 45.5%) as an yellow oil which was used for the next step without further purification.

Step 4

Method was as described for Example 5 but using (R,S)-[(2N-adamantyloxycarbonyl-3-methyl)-9H-1,2,3,4-tetrahydro-β-carboline-3-yl]-carboxylic acid (526 mg, 1 mmol) from Example 1, step 3, and the amine from step 3. The crude residue was chromatographed on silica gel using cyclohexane/ethyl acetate 80:20% to isolate the ester (100 mg, 15.0%) as a pale yellow solid from n-pentane.

Step 5

A solution of the carboxylic acid ester from step 4 (80 mg, 0.1 mmol) in a mixture of dioxane/water =1:1 (5 mL) was treated with LiOH (8 mg, 0.4 mmol) and the reaction mixture was stirred for 4 days. The solution was diluted with ethyl acetate (50 mL) and acidified with 7.5% citric acid solution, the organic layer was separated, dried over Na$_2$SO$_4$, evaporated in vacuo and the product was isolated as a beige solid upon drying (40 mg, 45%). mp: 133°–138° C.

EXAMPLE 21

1,3,4,9-Tetrahydro-3-methyl-3-[[2-[[1-oxo-3-(1H-tetrazol-5-yl)propyl]amino]-2-phenethyl]amino]-carbonyl]-2H-pyrido3,4-b]indole-2-carboxylic acid, tricyclo[3.3.1.1$^{3,7}$]dec-2-yl ester

Step 1

A solution of 3-(1-benzyl-tetrazol-5-yl)propionic acid (9.1 g, 39.2 mmol) (preparation described in EP 405 537)

in ethanol (50 mL) was treated with 20% palladium on carbon (1.0 g) and placed under an atmosphere of hydrogen at 80 bar and 40° C. with agitation. After 24 hours the reaction mixture was filtered, concentrated in vacuo and treated with ether to isolate the product as white crystals (3.8 g, 68%).

Step 2

To a stirred suspension of the carboxylic acid from step 1 was added successively pentafluorophenol (70 mg, 0.4 mmol), N,N'-dicyclohexylcarbodiimide (80 mg, 0.4 mmol) and 1-hydroxybenzotriazole hydrate. After stirring for 4 hours at room temperature a solution of the amino compound (200 mg, 0.4 mmol), prepared in Example 8, was added and the reaction mixture was stirred for another 16 hours, then filtered and evaporated in vacuo. The residue was chromatographed on silica gel using ethyl acetate/ethanol (50%) as eluant to isolate the required product as a pale beige solid from ether (80 mg, 32.4%). mp: 250°-252° C.

EXAMPLE 22

3-[[2-[[(2-Carboxy-1-cyclopropyl)carbonyl]amino]-2-phenethyl]amino]carbonyl]-1,3,4,9-tetrahydro-3-methyl-2H-pyrido[3,4-b]indole-2-carboxylic acid ethyl ester, tricyclo[3.3.1.1$^{3,7}$]dec-2-yl ester Method was as described for Example 21 but using cyclopropane dicarboxylic acid mono ethyl ester (*J. Amer. Chem. Soc.* 1957, 79, 4994). The crude residue was chromatographed on silica gel using cyclohexane/ethyl acetate (50%) to yield the cyclopropane ethyl ester derivative as a pale beige solid from ether/n-pentane (200 mg, 39.5%). mp: 100°-106° C.

TABLE I

Structure: indole-based with substituents R¹, R², R³, R⁴, R⁹, R¹², R¹³, R¹⁴, Ar, and A linker, with formula showing $R^2$-CO-N(R^9)-C(R^{12})(R^{13})-C(R^3)(R^4)-Ar$ and N-A-R¹ linkage.

| No. | R¹ | A | R² | R³ | R⁴ | Ar | R⁹ | R¹² | R¹³ |
|---|---|---|---|---|---|---|---|---|---|
| 1 (D,L) | 1-Adamantyl | —CO—O— | CH₃ | H | H | C₆H₅ | H | H | H |
| 2 (D) | " | —CO—O— | CH₃ | H | H | C₆H₅ | H | H | H |
| 3 (L) | " | —CO—O— | CH₃ | H | H | C₆H₅ | H | H | H |
| 4 (D,L) | " | —CO—O— | CH₃ | CH₂OH | H | C₆H₅ | H | H | H |
| 5 (D) | " | —CO—O— | CH₃ | CH₂OH | H | C₆H₅ | H | H | H |
| 6 (L) | " | —CO—O— | CH₃ | CH₂OH | H | C₆H₅ | H | H | H |
| 7 (D,L) | 2-Adam. | —CO—O— | CH₃ | CH₂—OH | OH | C₆H₅ | H | H | H |
| 8 (D,L) | " | —CO—O— | CH₃ | H | NH₂ | C₆H₅ | H | H | H |
| 9 (D,L) | " | —CO—O— | CH₃ | H | NH—C(=O)—CH₂—CH₂—COOH | C₆H₅ | H | H | H |
| 10 (L) | " | —CO—O— | CH₃ | H | NH—C(=O)—CH₂—CH₂—COOH | C₆H₅ | H | H | H |
| 11 (D,L) | " | —CO—O— | CH₃ | H | NH—C(=O)—CH₂—CH₂—C(=O)—O—CH₂—C₆H₅ | C₆H₅ | H | H | H |
| 13 (D,L) | " | —CO—O— | CH₃ | H | O—C(=O)—CH₂—CH₂—COOH | C₆H₅ | H | H | H |
| 14 (D,L) | " | —CO—O— | CH₃ | H | NH—C(=O)—CH₂—COOH | C₆H₅ | H | H | H |
| 15 (D,L) | " | —CO—O— | CH₃ | H | NH—C(=O)—CH=CH—COOH | C₆H₅ | H | H | H |

TABLE I-continued

[Structure shown at top of table: indole-containing compound with substituents R², R³, R⁴, R⁹, R¹², R¹³, R¹⁴, A, R¹, Ar]

| No. | R¹ | A | R² | R³ | R⁴ | Ar | R⁹ | R¹² | R¹³ |
|---|---|---|---|---|---|---|---|---|---|
| 16 (D,L) | " | —CO—O— | CH₃ | CH₂NHCCH₂CH₂CO₂H<br>∥<br>O | H | C₆H₅ | H | H | H |
| 17 (D,L) | " | —CO—O— | H | H | H | C₆H₅ | H | H | H |
| 18 (D,L) | t.butyl | —CO—O— | CH₃ | COOH | H | C₆H₅ | H | H | H |
| 19 (D,L) | " | —SO₂—NH— | CH₃ | H | H | C₆H₅ | H | H | H |
| 20 (D,L) | " | —CO—O— | CH₃ | CH₂CO₂H | H | C₆H₅ | H | H | H |
| 21 (D,L) | " | —CO—O— | CH₃ | H | $-\text{N}-\text{C}-\text{CH}_2-\text{CH}_2-\text{C}\overset{N=N}{\underset{\underset{H}{N-N}}{\diagup}}$<br>H  O | C₆H₅ | H | H | H |
| 22 (D,L) | " | —CO—O— | CH₃ | H | NH—C—CH—CH—COOH<br>    ∥            |<br>    O            CH₂ | C₆H₅ | H | H | H |

We claim:
1. A compound of the formula

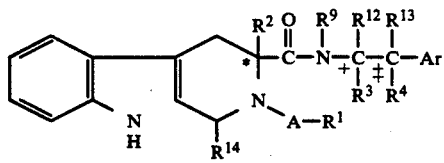

or a pharmaceutically acceptable salt thereof wherein:
$R^1$ is 2-adamantyl or tert.-butyl;
A is —OCO—;
$R^2$ is H or —$CH_3$;
$R^3$ is H, —$CH_2OH$, —COOH, —$CH_2NH$-$COCH_2CH_2CO_2H$;
$R^4$ is

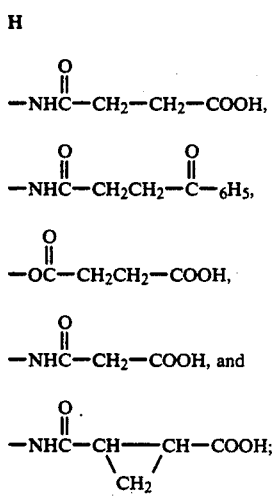

$R^9$ is hydrogen or methyl;
$R^{14}$ is hydrogen;
Ar is phenyl.

2. A compound named (+/−)1,3,4,9-tetrahydro-3-methyl-3-[[2-phenylethyl)-amino]carbonyl]-2H-pyrido[3,4-b]indole-2-carboxylic acid, tricyclo[3.3.2.2$^{3,7}$]dec-2-yl ester.

3. A compound named (R)-1,3,4,9-tetrahydro-3-methyl-3-[[2-phenylethyl)amino]carbonyl]-2H-pyrido[3,4-b]indole-2-carboxylic acid, tricyclo[3.3.1.1$^{3,7}$]dec-2-yl ester.

4. A compound named (S) 1,3,4,9-tetrahydro-3-methyl-3-[[2-phenylethyl)amino]carbonyl]-2H-pyrido[3,4-b]indole-2-carboxylic acid, tricyclo[3.3.1.1$^{3,7}$]dec-2-yl ester.

5. A compound named 1,3,4,9-tetrahydro-3-[[[1-(hydroxymethyl)-2-phenylethyl]amino]carbonyl]-3-methyl-2H-pyrido-[3,4-b]indole-2-carboxylic acid, tricyclo-[3.3.1.1$^{3,7}$]dec 2-yl ester (mixture of diastereomers).

6. A compound named (R)-1,3,4,9-tetrahydro-3-[[[1-(hydroxymethyl)-2-phenylethyl]amino]carbonyl]-3-methyl-2H-pyrido[3,4-b]indole-2-carboxylic acid,tricyclo[3.3.1.1$^{3,7}$]dec-2-yl ester.

7. A compound named (S)-1,3,4,9-tetrahydro-3-[[[1-(hydroxymethyl)-2-phenylethyl]amino]carbonyl]-3-methyl-2H-pyrido-[3,4-b]indole-2-carboxylic acid, tricyclo[3.3.1.1$^{3,7}$]dec-2-yl ester.

8. A compound named 1,3,4,9-tetrahydro-3-[[[1-(hydroxymethyl)-2-hydroxy-2-phenylethyl]amino]carbonyl]-3-methyl-2H-pyrido-[3,4-b]indole-2-carboxylic acid, tricyclo[3.3.1.1$^{3,7}$]dec-2-yl ester.

9. A compound named 3-[[(2-amino-2-phenylethyl)amino]carbonyl]-1,3,4,9-tetrahydro-3-methyl]-2H-pyrido[3,4-b]indole-2-carboxylic acid, tricyclo[3.3.1.1$^{3,7}$]dec-2-yl ester, (mixtures of diastereomers).

10. A compound named 3-[[[2-(3-carboxy-1-oxopropyl)-amino]-2-phenylethyl]amino]carbonyl]-1,3,4,9-tetrahydro-3-methyl-2H-pyrido[3,4-b]indole-2-carboxylic acid, tricyclo[3.3.1.1$^{3,7}$]dec-2-yl ester, [R-(R*,R*)] and [R-(R*,S*)]-.

11. A compound named 3-[[[2-(R)-(3-carboxy-1-oxopropyl)amino]-2-phenylethyl]amino]carbonyl]-1,3,4,9-tetrahydro-3-(S)-methyl-2H-pyrido[3,4-b]indole-2-carboxylic acid, tricyclo[3.3.1.1$^{3,7}$]dec-2-yl ester.

12. A compound named 3-[3-[3-[2-[2-[1,4-dioxo-4-(phenylmethoxy)butyl]amino]-2-phenylethyl]amino]-carbonyl]-1,3,4,9-tetrahydro-3-methyl]-2H-pyrido[3,4-b]indole-2-carboxylic acid, tricyclo[3.3.1.1$^{3,7}$]dec-2-yl ester (mixture of diastereomers).

13. A compound named 3[[(2-hydroxy-2-phenylethyl)amino]carbonyl]-1,3,4,9-tetrahydro 3-methyl]-2H-pyrido[3,4-b]indole-2-carboxylic acid, tricyclo[3.3.1.1$^{3,7}$]dec-2-yl ester.

14. A compound named butanedioic acid,mono[2-[[[2,3,4,9-tetrahydro-3-methyl-2-[(tricyclo[3.3.1.1$^{3,7}$]-dec-2-ylox)carbonyl]-1H-pyrido[3,4-b]indole-3-yl]carbonyl]amino]-1-phenethyl] ester.

15. A compound named 3-[[[2-[(3-carboxyacetyl)amino]-2-phenethyl]-amino]-carbonyl]-1,3,4,9-tetrahydro-3-methyl-2H-pyrido-[3,4-b]indole-2 carboxylic acid, [tricyclo[3.3.1.1$^{3,7}$]dec-2-yl ester (mixture of diastereomers)

16. A compound named 3-[[[2-[(3-carboxy-1-oxo-2-propenyl)amino]2-phenethyl]amino]carbonyl]1,3,4,9-tetrahydro-3-methyl-2H-pyrido[3,4 b]indole-2-carboxylic acid, [tricyclo[3.3.1.1$^{3,7}$]dec-2-yl ester (mixture of diastereomers).

17. A compound named 3-[[[1-[[(3-carboxy-1-oxopropyl)amino]methyl]-1-phenethyl]amino]carbonyl]-1,3,4,9-tetrahydro-3-methyl-2H-pyrido[3,4-b]indole-2-carboxylic acid, [tricyclo[3.3.1.1$^{3,7}$]dec-2-yl ester (mixture of diastereomers).

18. A compound named (+/−)-1,3,4,9-tetrahydro-3-[[(2-phenethyl)amino-]carbonyl]-2H-pyrido[3,4 b]indole-2-carboxylic acid, [tricyclo[3.3.1.1$^{3,7}$]dec-2-yl ester.

19. A compound named 3-[[[3-carboxy-1-(phenylmethyl)propyl]amino]-carbonyl]-1,3,4,9-tetrahydro-3-methyl-2H-pyrido-[3,4-b]indole-2-carboxylic acid, tricyclo-[3.3.1.1$^{3,7}$]dec-2-yl ester.

20. A compound named 3-[[[2-[[(2-carboxy-1cyclopropyl)carbonyl]amino]-2-phenethyl]amino]carbonyl]-1,3,4,9-tetrahydro-3-methyl-2H-pyrido[3,4-b]indole-2-carboxylic acid ethyl ester, tricyclo[3.3.1.1$^{3,7}$]dec-2-yl ester.

21. A pharmaceutical composition comprising an effective amount of a compound according to claims 5, 18, 19, or 20 and a pharmaceutically acceptable carrier.

* * * * *

UNITED STATES PATENT AND TRADEMARK OFFICE
CERTIFICATE OF CORRECTION

PATENT NO. : 5,244,905
DATED : September 14, 1993
INVENTOR(S) : Horwell, et al

It is certified that error appears in the above-indentified patent and that said Letters Patent is hereby corrected as shown below:

Column 51, line 4, at right margin, insert "I".

Column 51, line 26, insert "C" before the subscript "6".

Column 51, line 46, delete "2" two times inside brackets and insert instead "1" two times.

Column 52, line 26, insert "-" before the last "3".

Column 52, line 35, insert "-" after the last "2".

Column 52, line 39, insert "-" before the "2".

Column 52, line 40, insert "-" after the "4".

Column 52, line 49, insert "-" after the "4".

Signed and Sealed this

Twenty-second Day of March, 1994

Attest:

BRUCE LEHMAN

Attesting Officer       Commissioner of Patents and Trademarks

UNITED STATES PATENT AND TRADEMARK OFFICE
CERTIFICATE OF CORRECTION

PATENT NO. : 5,244,905
DATED : September 14, 1993
INVENTOR(S) : Horwell, et al.

It is certified that error appears in the above-identified patent and that said Letters Patent is hereby corrected as shown below:

Column 52, line 36, delete the first "[".

Column 52, line 41, delete the first "[".

Column 52, line 46, delete the first "[".

Column 52, line 50, delete the first "[".

Signed and Sealed this

Seventeenth Day of May, 1994

Attest:

BRUCE LEHMAN

Attesting Officer   Commissioner of Patents and Trademarks